United States Patent
De Groot et al.

(10) Patent No.: US 10,582,683 B2
(45) Date of Patent: Mar. 10, 2020

(54) TRIPLOID WATERMELON PLANTS WITH A BUSH GROWTH HABIT

(71) Applicant: NUNHEMS B.V., Nunhem (NL)

(72) Inventors: Erik De Groot, Nonantola (IT); Elena Chiapparino, Bologna (IT); Richard Bernard Berentsen, Heythuysen (NL)

(73) Assignee: NUNHEMS B.V., Nunhem (NL)

( * ) Notice: Subject to any disclaimer, the term of this patent is extended or adjusted under 35 U.S.C. 154(b) by 300 days.

(21) Appl. No.: 15/360,749

(22) Filed: Nov. 23, 2016

(65) Prior Publication Data

US 2017/0156278 A1 Jun. 8, 2017

Related U.S. Application Data

(60) Provisional application No. 62/262,107, filed on Dec. 2, 2015.

(51) Int. Cl.
*A01H 6/34* (2018.01)
*A01H 5/08* (2018.01)
*A01H 1/04* (2006.01)

(52) U.S. Cl.
CPC ............... *A01H 6/342* (2018.05); *A01H 1/04* (2013.01); *A01H 5/08* (2013.01)

(58) Field of Classification Search
CPC .................................. A01H 5/08; A01H 6/342
See application file for complete search history.

(56) References Cited

U.S. PATENT DOCUMENTS

| | | |
|---|---|---|
| 6,355,865 B1 | 3/2002 | Elmstrom |
| 7,115,800 B2 | 10/2006 | Barham et al. |
| 7,164,059 B2 | 1/2007 | Barham |
| 7,314,979 B2 | 1/2008 | Lanini et al. |
| 8,034,999 B2 | 10/2011 | Lanini et al. |
| 2003/0172414 A1 | 9/2003 | Zhang et al. |
| 2006/0168701 A1 | 7/2006 | Zhang et al. |
| 2008/0005814 A1 | 1/2008 | Zhang |
| 2008/0163388 A1 | 7/2008 | Zhang |
| 2008/0244764 A1 | 10/2008 | Barham |

FOREIGN PATENT DOCUMENTS

| | | |
|---|---|---|
| WO | 03075641 A2 | 9/2003 |
| WO | 2012069539 A1 | 5/2012 |

OTHER PUBLICATIONS

Ma et al (Acta Agriculturae Shanghai, 2004, 20 (3): 58-61) + English translation (Year: 2004).*
Maynard (Acta Agriculturae 318, 1992. 169-178) (Year: 1992).*
Yang et al (Cucurbit Genetics Cooperative Report 31-32:11-14 (2008-2009) (Year: 2009).*
Allen et al., "Transcript-specific, single-nucleotide polymorphism discovery and linkage analysis in hexaploid bread wheat (*Triticum aestivum* L.)", Plant Biotechnology J. (2011), vol. 9: 1086-1099.
"Watermelon genome sequence," Cucurbit Genomics Database, http://www.icugi.org/cgi-bin/ICuGI/index.cgi, Retrieved Mar. 9, 2017, p. 1 of 1.
Eigsti, Hort Science (1971) vol. 6: 1-2.
Guner, et al., "The Genes of Watermelon," HortScience (2004) vol. 39(6): 1175-1182.
Guo, et al., "The draft genome of watermelon (*Citrullus lanatus*) and resequencing of 20 diverse accessions," Nature Genetics (2013), vol. 45: 51-58.
Henikoff, et al., "Amino acid substitution matrices from protein blocks," Procl. Natl. Acad. Sci. (1992) vol. 89: 10915-10919.
Kihara, "Triploid Watermelons," Proceedings of American Society for Horticultural Science (1951) vol. 58: 217-230.
Sari,et al., "Comparison of ploidy level screening methods in watermelon: *Citrullus lanatus* (Thunb.) Matsum. and Nakai," Scientia Horticulturae (1999) vol. 82: 265-277.
Wolukau, et al., "Identification of Amplified Fragment Length Polymorphism Markers Linked to Gummy Stem Blight (*Didymella bryoniae*) Resistance in Melon (*Cucumis melo* L.) PI 420145," HortScience (2009) vol. 44(1): 32-34.
Li, Y., et al., "Genetic Analysis of a Dwarf Vine and Small Fruit Watermelon Mutant", Horticultural Plant Journal, vol. 2, No. 4, pp. 224-228; Jul. 2016.

* cited by examiner

*Primary Examiner* — Lee A Visone
(74) *Attorney, Agent, or Firm* — Arent Fox LLP

(57) ABSTRACT

The application relates to the field of plant breeding, in particular watermelon breeding. Provided are bush type, triploid watermelon plants (and seeds from which these plants can be grown) and seedless watermelon fruits produced by these plants. Also provided are bush type pollenizer plants and bush type tetraploid plants and methods for producing triploid hybrids having a bush growth type, as well as methods for producing seedless watermelon fruits of high quality.

21 Claims, 2 Drawing Sheets
Specification includes a Sequence Listing.

Chr09

TRIPLOID WATERMELON PLANTS WITH A BUSH GROWTH HABIT

CROSS-REFERENCE TO RELATED APPLICATIONS

This application is a non-provisional U.S. patent application, which claims priority to U.S. provisional Application No. 62/262,107, filed Dec. 2, 2015. The disclosure of the priority application is incorporated in its entirety herein by reference.

BACKGROUND

Field of the Invention

The present invention relates to the field of plant breeding and plant improvement. Provided are new hybrid watermelon plants and seeds from which such plants can be grown, which are "bush" in growth habit (comprising the recessive "bush gene", designated "b") and triploid (2n=3x=33) in their chromosomal makeup. When these triploid hybrid plants are pollinated with normal diploid (2n=2x=22) pollen (obtainable from pollenizers), these plants produce triploid, seedless fruit of high quality. As the triploid hybrid plant has a bush growth habit, having short longest vines (equal to or below 150 cm, more preferably equal to or below 140 cm, especially equal to or below 100 cm) and short internode length, this plant can be grown at a higher density in the field compared to traditional non-bush triploid watermelon hybrids, leading to a higher fruit yield per hectare compared to triploid hybrids with normal growth habit (having an average longest vine length of above 200 or above 300 cm). The average plant diameter of a triploid bush plant according to the invention is equal to or below 300 cm, preferably 280 cm, especially equal to or below 200 cm, while other characteristics, such as leaf size and fruit size are similar to that of normal growth type triploid watermelon plants. Also provided are inbred diploid bush watermelon plants (bb) and inbred tetraploid (2n=4x=44) bush watermelon plants (bbbb), which are used as male and female parent, respectively, in order to produce the triploid bush hybrid watermelon plants (bbb) according to the invention. In addition triploid, seedless fruit, obtainable from the triploid bush plants according to the invention, are provided, as are seeds from which the triploid bush hybrid plants can be grown. Further a method for breeding triploid bush hybrids and methods for cultivating triploid bush hybrids are provided.

Description of Related Art

Seedless watermelon (*Citrullus lanatus* (Thunb.) Matsum. And Nak.) are produced by using pollen from diploid male parent plants to fertilize flowers of tetraploid maternal parent plants. Pollination of the tetraploid flowers with diploid pollen leads to hybrid F1 seeds which are triploid (Kihara, 1951, Proceedings of American Society for Horticultural Science 58: 217-230; Eigsti 1971, Hort Science 6: 1-2). The triploid hybrid plants grown from these F1 seeds are self-infertile as they produce sterile pollen due to chromosome imbalance (Fehr, 1987). The triploid hybrids, therefore, need to be pollinated by a diploid pollenizer to produce watermelon fruit. Triploid plants are, therefore, interplanted with pollenizer plants for fruit production. The "seedless" fruit produced after pollination on the triploid hybrid plant are not truly seedless, but often contain some undeveloped, small, pale seeds, which are edible.

For optimal fruit set, sufficient viable pollen is required. Plants are generally planted at a ratio of 1 pollenizer per every 2-4 triploid plants. Triploid plants and pollenizers are either planted in separate rows (e.g. 1 row of pollenizer and 2-4 rows of triploids), or interplanted within rows (e.g. planting 1 pollenizer plant in between 2 to 3 triploid plants in the same row), or interplanted in narrow rows between rows of triploids (see US 2006/0168701 Table 2). The fruit produced on the pollenizer plants preferably has a different rind pattern from the fruit on the triploid hybrids, so that these can be easily distinguished.

Some problems remain with seedless watermelon production, such as the production of the tetraploid mother line (chromosome doubling through colchicines treatment of seedlings), finding compatibility between diploid pollenizer and tetraploid mother plants and triploid seeds often have a thicker seed coat, which decreases their vigor and germination. Fruit quality and uniformity is also often a problem, as are the high production costs of triploid seeds due to the above requirements.

Making a stable, tetraploid inbred mother line with the desired trait(s) is not straight forward, as it is not as simple as selecting a good diploid and doubling the chromosomes using e.g. colchicines treatment. After some cells with doubled chromosomes are obtained and a plant is regenerated, a number of generations of self pollination (inbreeding) are needed to stabilize (fix) the tetraploid and to eliminate undesired chromosomal aberrations.

Compact (or dwarf) diploid pollenizer plants having shorter vines and/or shorter internodes are often used to induce seedless-fruit set on normal (non-dwarf) hybrid triploid female parents and/or to produce seed-comprising fruit on the pollenizer plant itself. For example the variety Side Kick (Harris Morin) is used as pollenizer for normal hybrid triploids (seedless) and/or pollenizer fruit production (seeded). Side Kick is a diploid pollenizer comprising the recessive allele hmbn (U.S. Pat. No. 7,314,979 B2) in homozygous form, which leads to more branching (multi-branching) and thereby more "compact" diploid pollenizer plants. Also the diploid pollenizer fruits of homozygous hmbn hmbn plants are smaller than normal fruits (1.6 kg compared to 8.98 kg of a normal diploid). On the other hand, the triploid, seedless fruit produced when a normal hybrid triploid is pollinated with a pollenizer such as Side Kick are large, seedless fruit of 13-21 pounds (5.8-9.5 kg). The HMBN compact type (hmbn hmbn) is not as compact as the known diploid dwarf mutants (dw-1 dw-1, such as variety Bush Jubilee or dw-2 dw-2, such as variety J86), but is more compact than the standard diploid types (e.g. Allsweet), see Table 1 of U.S. Pat. No. 7,314,979 and Table 1 of U.S. Pat. No. 8,034,999. The HMBN compact type (hmbn hmbn) has many more secondary branches (average 44.9) than a normal diploid (average 14.7) or than a known dwarf diploid (average 19.3 and 7.3), while the internode length is longer (average 4.4 cm) than in the known dwarf diploids (average 3.4 and 4.1 cm), but shorter than in normal type diploids (average 7.2 cm).

U.S. Pat. No. 7,164,059 describes a short-vine, diploid pollenizer and its use to pollinate normal growth habit (normal growth type) triploid hybrids. The short-vine pollenizer is described as having an average internode length of less than 3 inches (less than 7.6 cm) and/or a plant diameter of less than 1.8 meter. By using a short-vine pollenizer in combination with normal habit triploids it is stated that 33% to 50% more triploids per acre can be planted (about 2000 triploids per acre, plus 400 to 1200 diploid pollenizers per acre; this equals about 4942 triploids per hectare, plus 988 to 2965 diploid pollenizers per hectare).

U.S. Pat. No. 7,115,800 describes the production of seedless watermelon fruit having an average weight of less than 5.4 kg (3.6 to 4.0 kg). The triploid watermelon plants are produced using "small" inbred tetraploid and "small" inbred diploid parental lines, whereby "small" refers to the fruit size and not to the plant size. The triploid hybrid plants, producing small fruit, have a normal growth type, with vine lengths of 320 cm or more and internode lengths of 8 or more cm.

US 2008/0005814 and US 2008163388 describe the development of a tetraploid watermelon plant, which is suitable as a female parent in triploid hybrid production having small, seedless fruit. The tetraploid plant has a normal vegetative growth habit. When pollinated with a diploid pollenizer, small fruit (1.5 to 2.5 kg) are produced.

US2008/0244764 describes a tetraploid watermelon line of normal growth type developed from the diploid Calsweet.

US 2006/0168701 and US 2003/0172414 describe diploid pollenizers ("Super Pollenizers") useful for pollinating triploid plants, thereby initiating fruit set of triploid, seedless fruit. The pollenizer has small leaves 5 to 12 times less than the surface area of a typical diploid pollenizer such as Sangria) and can be grown in close proximity of the normal type triploid hybrid. The pollenizer is heavily branched (lacy vined or open vines) and reduces the space, nutrients and light needed, leaving more space, nutrients and light for the triploid hybrid plants. According to the patent application 25% to 33% more seedless watermelons are produced per acre using this pollenizer.

U.S. Pat. No. 6,355,865 B1 describes a pollenizer plant having at least two of the features selected from (a) distinguished fruit phenotype, (b) high number of male flowers, (c) continued flowering, (d) early flowering and/or (e) modified plant morphology an growth habit, having more slender vines. As the diploid pollenizer is more slender and produces more flowers it may be planted in a 1:3 to 1:5 ratio (pollenizer:triploid hybrid), rather than the usual 1:2 ratio.

Besides the hmbn (mutlibranching) mutation described above, also four other genes have been described which lead to dwarf/compact plant habit in diploid watermelons when the mutant allele is present in homozygous form. These are named dw-1, dw-1$^s$ (allelic to dw-1), dw-2 and dw-3 (Guner and Wehner 2004, Hort Science 39(6): 1175-1182). Some of these mutants have been used to develop dwarf or short-vined diploid pollenizers, such as Bush Jubilee.

However, it has so far not been possible to produce triploid bush hybrid plants, which are capable of producing seedless fruits of high quality.

SUMMARY

It is an object of the invention to provide triploid hybrids which have a bush growth habit and produce seedless fruit of high quality. It is also an object of the invention to provide methods for producing such triploid hybrid plants and/or triploid fruits.

Bush triploid plants take less space in the field and can be grown in closer proximity to each other and/or to the pollenizers compared to normal type triploids, such as Boston F1 or Fashion F1. At least 1.5 times, 1.7 times, 2 times, 2.5 times or even 3 times as many bush triploid plants can be grown per hectare compared to non-bush (normal growth habit) watermelon triploid hybrids, such Boston F1 or Fashion F1. As the bush triploid plants have a reduced plant diameter but without affecting leaf size or fruit size, higher triploid fruit yields per hectare can be achieved. Using the triploid bush hybrids according to the invention at least about 1.25 times, preferably at least about 1.5 times as many fruits per hectare are produced compared to normal type triploid hybrids.

In one embodiment also a method for breeding bush triploid watermelon plants (bbb) is provided, as well as a method for cultivating bush triploid watermelon plants in commercial, seedless fruit production.

Also seeds from which triploid hybrid bush plants can be grown are encompassed herein, as are plant parts, in vitro propagations, cell or tissue cultures, harvested fruits, etc.

In another embodiment tetraploid bush plants and seeds from which such tetraploid bush plants can be grown are provided herein, as well as plant parts (cells, pollen, anthers, ovules, flowers, etc.) and in vitro propagations of such plants.

DETAILED DESCRIPTION OF A PREFERRED EMBODIMENT

Figure 1:
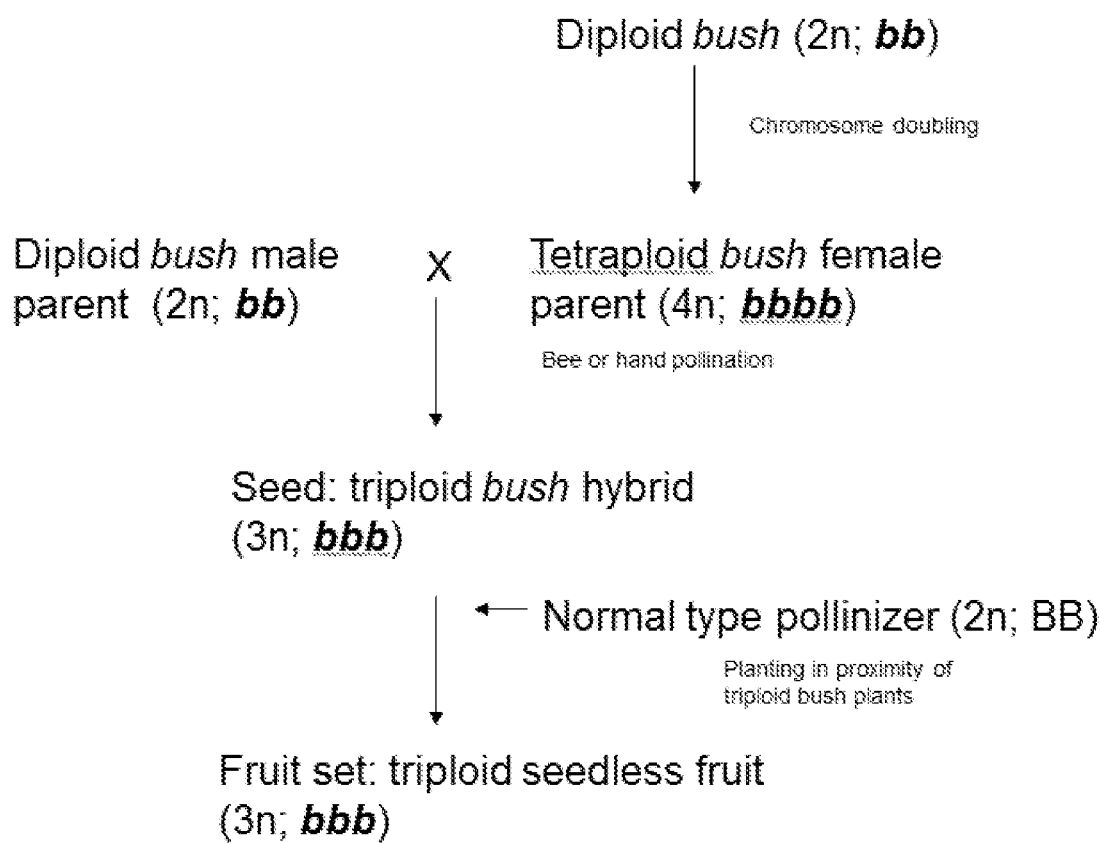
FIGS. 1-2 depict embodiments of the present disclosure.

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells plants, etc. Similarly, "a fruit" or "a plant" also refers to a plurality of fruits and plants.

As used herein, the term "plant" includes the whole plant or any parts or derivatives thereof, preferably having the same genetic makeup as the plant from which it is obtained, such as plant organs (e.g. harvested or non-harvested fruits, leaves, flowers, anthers, etc.), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants, such as plant cuttings, embryos, pollen, anthers, ovules, fruits (e.g. harvested tissues or organs), flowers, leaves, seeds, clonally propagated plants, roots, stems, root tips, grafts (scions and/or root stocks) and the like. Also any developmental stage is included, such as seedlings, cuttings prior or after rooting, etc.

As used herein, the term "variety" or "cultivar" means a plant grouping within a single botanical taxon of the lowest known rank, which can be defined by the expression of the characteristics resulting from a given genotype or combination of genotypes.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (loci plural) means a specific place or places or a site on a chromosome where for example a gene or genetic marker is found.

"Diploid plant" refers to a plant, vegetative plant part(s), or seed from which a diploid plant can be grown, having two sets of chromosome, designated herein as 2n.

"Triploid plant" refers to a plant, vegetative plant part(s), or seed from which a triploid plant can be grown, having three sets of chromosomes, designated herein as 3n.

"Tetraploid plant" refers to a plant, vegetative plant part(s), or seed from which a tetraploid plant can be grown, having four sets of chromosomes, designated herein as 4n.

"Pollenizer plant" or "pollenizer" refers to the (inbred or hybrid) diploid plant, or parts thereof (e.g. its pollen or scion), suitable as pollenizer for inducing fruit set on triploid plants. A pollenizer plant is, thus, able to lead to good fruit set (and good triploid fruit yield) of triploid plants, by producing an appropriate amount of pollen at the appropriate day-time and for an appropriate period of time.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 3, 4, 5, 6, 7 or more) of inbreeding, resulting in a plant line with a high uniformity.

"Male parent" refers to the pollenizer plant used as male parent for inducing fruit set and seed production on a tetraploid female parent, resulting in F1 hybrid triploid seeds. Both the male parent and the female parent are inbred so that each parent is nearly homozygous and stable. "Female parent" or "tetraploid parent" refers to the plant which is pollinated with pollen of the male parent, leading to the production of fruits containing triploid seeds. The female parent is inbred so that it is nearly homozygous and stable.

"Hybrid triploid plant" or "F1 triploid" is a triploid plant grown from hybrid, triploid seed obtained from cross fertilizing a male diploid parent with a female tetraploid parent.

"Seedless fruit" are triploid fruit which contain no mature seeds. The fruit may contain one or more small, edible, white ovules.

"Interplanting" refers to the combination of two or more types of seeds and/or transplants sown or transplanted on the same field, especially the sowing and/or transplanting of pollenizers in the same field as triploid hybrid plants (for seedless fruit production on the triploid plants and diploid fruit production on the pollenizer plants). For example, the pollenizer may either be planted in separate rows or interplanted with the triploid plants in the same row (e.g. in hills within each row). Pollenizers may also be planted in between rows of triploids. Also seeds of pollenizers and triploid hybrids may be mixed prior to seeding, resulting in random seeding. The transplants of the triploid hybrid plants and/or pollenizer plants may also comprise a rootstock of a different plant. Suitable rootstocks are known in the art. Watermelon plants with a different rootstock are referred to as "grafted".

"Planting" or "planted" refers to seeding (direct sowing) or transplanting seedlings (plantlets) into a field by machine or hand.

"Vegetative propagation" refers to propagation of plants from vegetative tissue, e.g. by in vitro propagation or grafting methods (using scions). In vitro propagation involves in vitro cell or tissue culture and regeneration of a whole plant from the in vitro culture. Grafting involves propagation an original plant by grafting onto rootstock. Clones (i.e. genetically identical vegetative propagations) of the original plant can thus generated by either in vitro culture or grafting.

The term "gene" means a (genomic) DNA sequence comprising a region (transcribed region), which is transcribed into a messenger RNA molecule (mRNA) in a cell, and an operably linked regulatory region (e.g. a promoter). Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

The term "locus" (loci plural) means a specific place or places or a site on a chromosome where for example a gene or genetic marker is found. The bush locus (or bush growth-type conferring locus) is, thus, the location in the genome of watermelon, where the bush allele is found. The locus is on cultivated watermelon chromosome 9 (using the chromosome assignment of the published watermelon genome found on the world wide web at icugi.org/cgi-bin/ICuGI/index.cgi under "Watermelon: Genome", "Watermelon genome (97103)—version 1" and as described in Guo S, Zhang J, Sun H, Salse J, Lucas W, Zhang H, Zheng Y, Mao L, Ren Y, Wang Z (2013) "The draft genome of watermelon (*Citrullus lanatus*) and resequencing of 20 diverse accessions" (Nature Genetics 45:51-58).

"Recessive" refers to an allele which expresses its phenotype when no functional dominant allele is present in the genome. The recessive bush allele (b) according to the invention, as found in (and obtainable from) NCIMB accession numbers provided herein, results in a bush growth habit when present in two copies in a diploid plant (bb), in four copies in a tetraploid plant (bbbb) or in three copies in a triploid plant (bbb), whereby a functional dominant Bush allele (B) is absent in these plants. The B allele is thus essentially the wild type, non-mutated allele, found in plants lacking the mutant b allele.

"Bush type" or "bush growth type" or "bush growth habit" or "bush habit" refers to the heritable (genetically determined by the bush allele) vegetative growth habit of a plant line or variety at maturity having an average internode length of about 7 cm or less (but at least about 4.7 cm, preferably at least about 5.0 cm) and an average longest vine length of about 150 cm or less, about 140 cm or less, about 130 cm or less, preferably about 100 cm or less (but at least about 70 cm). Also the average leaf size is not reduced by the bush allele and is at least about 11 cm length and/or 15 cm width or larger. A "non-bush" growth type is any other type (having a B allele), such as normal triploid growth types (e.g. Fashion F1 or Boston F1) producing an average longest vines of significantly more than 100 cm, for example generally more than 200 cm or more than 300 cm (see also the Examples).

"Longest vine length" or "average longest vine length" refers to the average length of the longest vine of a plurality of plants of a watermelon line or variety, when these are fully grown (at maturity). The longest vine may herein also be referred to as the stem (thus, "stem" and "longest vine" are used interchangeably herein).

"Plant diameter" refers to the average diameter of a plurality of plants of a watermelon line or variety when fully grown, i.e. the diameter from the tip of the longest vine on one side of the plant to the tip of the longest vine on the other side of the plant.

"Internode length" refers to the average length of the internodes on a vine of a plurality of plants of a specific line or variety.

"Internode number" refers to the average number of internodes on a vine, e.g. on the longest vine.

"Backcrossing" is a process whereby hybrid progeny, for example an F1 hybrid, is repeatedly crossed back to one of the parents of the hybrid. Backcrossing can be used to introduce one or several single locus conversions from one background to another.

Throughout this document "average" and "mean" are used interchangeably and refer to the arithmetic mean.

"Single gene conversion" or "single gene converted" refers to plants developed by backcrossing, wherein essentially all the desired morphological and physiological characteristics of a plant (e.g. an inbred) are retained in addition to a single gene transferred into the plant via backcrossing or genetic engineering.

"Cultivated watermelon" refers herein to *Citrullus lanatus* and having good agronomic characteristics, especially producing marketable fruits of good fruit quality and fruit uniformity.

"Yield" means the total weight of all watermelon fruits harvested per hectare of a particular line or variety.

"Marketable yield" means the total weight of all marketable watermelon fruits, especially seedless triploid fruit of at least 2.5 kg, harvested per hectare of a particular line or variety, i.e. fruits suitable for being sold for fresh consumption, having good flavour (no off-flavours), at least 10% brix and flesh color properties and no deficiencies such as hollow heart.

"Allelism test" refers to a genetic test whereby it can be tested whether two phenotypes seen in two plants are determined by the same gene or by different genes. For example, if a homozygous diploid bush plant (bb) is crossed with another watermelon plant that is homozygous for a different recessive gene, at a different locus (e.g. the hmbn allele determining multibranching), the F1 plant will not have the bush growth type and not the multibranching phenotype and the F2 generation will segregate for the two phenotypes (bush and multibranching) independently, in a ratio of 9:3:3:1, i.e. 9 (non-bush/non-multibranching): 3 (bush/non-multibranching): 3 (non-bush/multibranching):1 (bush/multibranching).

"SNP marker" refers to a Single Nucleotide Polymorphism between different watermelon lines or varieties. The SNP markers provided herein are closely linked to the recessive bush allele found in the seeds deposited. Thus, for example, SNP1 comprises a 'T' (Thymine) genotype at nucleotide position 30.382.688 of chromosome 9 and/or at nucleotide 76 of SEQ ID NO: 1 (or at the equivalent nucleotide of a sequence comprising at least 90%, 91%, 92%, 93%, 94%, 95%, 96%, 97% or more sequence identity to SEQ ID NO:1) when the recessive bush allele is present, and a 'C' (Cytosine) genotype when the bush allele is absent and the B allele (which may also be referred to as the Wild Type, WT, allele, i.e. the allele which confers the "non-bush" growth type or "normal" growth type) is present at that position on chromosome 9 and/or at nucleotide 76 of SEQ ID NO: 1 (or at nucleotide 76 the equivalent nucleotide of a sequence comprising at least 90%, 91%, 92%, 93%, 94%, 95%, 96%, 97% or more sequence identity to SEQ ID NO:1). Similarly, for example, SNP2 comprises an 'A' (Adenine) genotype at nucleotide position 30.770.924 of chromosome 9 and/or at nucleotide 76 of SEQ ID NO: 2 (or at the equivalent nucleotide of a sequence comprising at least 90%, 91%, 92%, 93%, 94%, 95%, 96%, 97% or more sequence identity to SEQ ID NO:2) when the recessive bush allele is present, and a 'G' (Guanine) genotype when the bush allele is absent and the B allele (which may also be referred to as the Wild Type, WT, allele, i.e. the allele which confers the "non-bush" growth type or "normal" growth type) is present at that position on chromosome 9 and/or at nucleotide 76 of SEQ ID NO: 2 (or at the equivalent nucleotide of a sequence comprising at least 90%, 91%, 92%, 93%, 94%, 95%, 96%, 97% or more sequence identity to SEQ ID NO:2). Thus, a diploid plant having a bush growth habit comprises two bush alleles and the genotype TT for SNP1 and/or the AA genotype for SNP2. Likewise a triploid plant having a bush growth habit comprises three bush alleles and the genotype TTT for SNP1 and/or the genotype AAA for SNP2. Likewise a tetraploid plant having a bush growth habit comprises four bush alleles and the genotype TTTT for SNP1 and/or the genotype AAAA for SNP2.

The "equivalent nucleotide of a sequence comprising at least 90%, 91%, 92%, 93%, 94%, 95%, 96%, 97% or more sequence identity to SEQ ID NO: 1 or SEQ ID NO: 2" refers to the SNP being present in a variant sequence at a nucleotide corresponding to the same nucleotide (e.g. corresponding to nucleotide 76 of SEQ ID NO: 1 or 2) in the variant sequence, i.e. in a sequence comprising at least 90%, 91%, 92%, 93%, 94%, 95%, 96%, 97%, 98% or 99% sequence identity to the mentioned SEQ ID NO. It may for example be that the variant sequence is one or a few nucleotides shorter, but when one pairwise aligns the variant sequence with the mentioned SEQ ID NO, one can see which nucleotide of the variant sequence corresponds to the same nucleotide. In the variant sequence this may for example be nucleotide number 75 or 77 of that variant sequence which corresponds to nucleotide 76 of the mentioned sequence.

The term "SNP genotype" refers to the nucleotide present at the particular SNP. When referring to the "bush genotype" or "bush SNP genotype", reference to the SNP nucleotide which is indicative of the presence of the recessive bush allele is made, i.e. a 'T' for SNP1 or a 'A' for SNP2. The term "SNP haplotype" refers to the nucleotide present at both the SNP1 and SNP2 locations. When referring to the "bush haplotype", reference to the SNP genotype of the SNP markers SNP1 and SNP2 physically linked to the bush allele is made, which comprises nucleotides T and A for SNP1 and SNP2, respectively.

The recessive bush allele, and the bush locus, is found in the region starting at 28 Mb of chromosome 9 and ending at 33 Mb of chromosome 9, in one aspect in the region starting at 28 Mb and ending at 32 Mb, in another aspect starting at 29 Mb and ending at 32 Mb, and in yet another aspect starting at 29 Mb and ending at 33 Mb of chromosome 9. See also FIG. 2.

"Cultivated watermelon genome" and "physical position on the cultivated watermelon genome" and "chromosome 3" refers to the physical genome of cultivated watermelon, world wide web at icugi.org/cgi-bin/ICuGrindex.cgi under "Watermelon: Genome", "Watermelon genome (97103)—version 1" and the physical chromosomes and the physical position on the chromosomes. So, for example SNP_01 is located at the nucleotide (or 'base') positioned physically at nucleotide 30.382.688 of chromosome 9, SNP_02 is located at the nucleotide (or 'base') positioned physically at nucleotide 30.770.924 of chromosome 9.

"Brix" or "degree Brix" or "° brix" refers to the mean total soluble solids content as measured on several mature fruits using a refractometer. Preferably the mean of at least three fruits, each measured between the centre and the rind of the cut-open fruit, is calculated.

"Marketable" in relation to fruit quality means that the watermelon fruits are suitable for being sold for fresh consumption, having good flavour (no off-flavours), a degree brix of at least 9.0, preferably at least 10.0 or at least 11.0 and preferably also a uniform fruit flesh color, being e.g. white (e.g. variety Cream of Saskatchewan), yellow (e.g. variety Yamato Cream 1), orange (e.g. variety Tendersweet), pink (e.g. variety Sadul), pinkish red (e.g. variety Crimson Sweet), red (e.g. variety Sugar Baby) or dark red (e.g. variety Dixie Lee).

"Uniform fruit flesh color" means that the color throughout the mature fruits, when cut open through the middle (midsection), is evenly distributed throughout the fruit flesh, i.e. not patchy. Thus, a red fruit is red throughout the fruit flesh and does not contain white patches. An example of a fruit with uniform red color is the diploid variety Premium F1 (Nunhems).

"Physical distance" between loci (e.g. between molecular markers and/or between phenotypic markers) on the same chromosome is the actually distance expressed in bases or base pairs (bp), kilo bases or kilo base pairs (kb) or megabases or mega base pairs (Mb).

"Uniformity" or "uniform" relates to the genetic and phenotypic characteristics of a plant line or variety. Inbred lines are genetically highly uniform as they are produced by several generations of inbreeding. Likewise, and the F1 hybrids and the triploid hybrids which are produced from such inbred lines are highly uniform in their genotypic and phenotypic characteristics and performance.

A genetic element or genetic determinant, a gene or allele or locus conferring a trait (such as the bush growth type) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as into a non-bush line or variety) using traditional breeding techniques without resulting in a phenotypic change of the recipient plant apart from the addition of the trait conferred by the genetic element, gene or allele or locus. The terms are used interchangeably and the genetic element, gene or allele or locus can, thus, be transferred into any other genetic background lacking the trait. Not only seeds deposited and comprising the genetic element, gene or allele or locus can be used, but also progeny/descendants from such seeds which have been selected to retain the genetic element, gene or allele, can be used and are encompassed herein, such as commercial varieties developed from the deposited seeds or from descendants or ancestors thereof. Likewise, other sources containing the genetic element, gene or allele or locus (e.g. the bush allele) can be identified and used to transfer it into other cultivated watermelon lines or varieties. Whether a plant (or genomic DNA, cell or tissue of a plant) comprises the same (or variant thereof) genetic element, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like, or combinations of techniques.

The term "marker assay" refers to a molecular marker assay which can be used to test whether on cultivated watermelon chromosome 9 a bush allele is present, by determining the genotype of any one or more markers physically linked to the bush allele, e.g. the genotype of SNP1 and/or SNP2 markers and/or another molecular marker linked physically to the bush allele. The step of "determining the genotype" may also be referred to as "genotyping". Optionally the marker assay may also include genotyping of other molecular markers linked to the bush allele, e.g. within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 and/or SNP2, i.e. either side of SNP1 and/or SNP2.

"Statistically significant" or "statistically significantly" different or "significantly" different refers to a characteristic of a plant line or variety that, when compared to a suitable control show a statistically significant difference in that characteristic (e.g. the p-value is less than 0.05, $p<0.05$, using ANOVA) from the (mean of the) control.

The term "traditional breeding techniques" encompasses herein crossing, backcrossing, selfing, selection, double haploid production, chromosome doubling, embryo rescue, protoplast fusion, marker assisted selection, mutation breeding etc., all as known to the breeder (i.e. methods other than genetic modification/transformation/transgenic methods).

"Backcrossing" refers to a breeding method by which a (single) trait, such as the bush growth type can be transferred from one (often an inferior) genetic background (also referred to as "donor") into another (often a superior) genetic background (also referred to as "recurrent parent"). An offspring of a cross (e.g. an F1 plant, or an F2 plant or F3 plant, etc., obtained from selfing the F1), is "backcrossed" to the parent with e.g. the superior genetic background. After repeated backcrossing, the trait of the one (often inferior) genetic background will have been incorporated into the other (often superior) genetic background.

"Marker assisted selection" or "MAS" is a process of using the presence of molecular markers (such as SNP markers), which are physically linked to a particular gene or allele (e.g. the recessive bush gene or allele), to select plants for the presence of the specific gene or allele. For example, a molecular marker physically linked to the bush gene or allele, can be used to detect and/or select watermelon plants, or plant parts, comprising the recessive bush gene or allele on chromosome 9. The closer the molecular marker to the locus, the less likely it is that the marker is dissociated from the locus through meiotic recombination. Likewise, the closer two markers are to each other the less likely it is that the two markers will be separated from one another (and the more likely they will co-segregate as a unit).

A molecular marker within 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of another marker refers to a marker which is physically located within the 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less, of the genomic DNA region flanking the marker, i.e. either side of the marker.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimising the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 92%, 95%, 98%, 99% or more (e.g. at least 99.1, 99.2 99.3 99.4, 99.5, 99.6, 99.7, 99.8, 99.9 or more (as determined by Emboss "needle" using default parameters, i.e. gap creation penalty=10, gap extension penalty=0.5, using scoring matrix DNAFULL for nucleic acids an Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 92%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) and Sambrook and Russell (2001).

In one aspect of the invention (seed of) a plant of the species *Citrullus lanatus* is provided, wherein said plant is triploid and has a bush growth habit (as defined herein). The plant comprising three copies of a recessive allele designated bush, wherein a representative sample of seed containing said allele has been deposited under accession numbers NCIMB 41907 (and/or NCIMB 41905 and NCIMB 41906). Ploidy can be easily determined by chromosome counting or flow cytometry or other known methods (Sari et al. 1999, Scientia Horticulturae 82: 265-277, incorporated herein by reference).

In another aspect a plant of the species *Citrullus lanatus*, wherein said plant is triploid and has a bush growth habit due to the presence of three copies of a recessive allele designated bush on chromosome 9, which allele is detectable by a thymine (T) at nucleotide 76 of SEQ ID NO: 1 or at the equivalent nucleotide of a sequence comprising at least 90%, 91%, 92%, 93%, 94%, 95%, 96%, 97% or more sequence identity to SEQ ID NO:1; and/or a adenine (A) at nucleotide 76 of SEQ ID NO: 2 or at the equivalent nucleotide of a sequence comprising at least 90%, 91%, 92%, 93%, 94%, 95%, 96%, 97% or more sequence identity to SEQ ID NO:2; and/or any other molecular marker which is within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which is physically linked to the bush allele. It was completely unexpected from the state of the art that any of the above characteristics would have been contributing or even related to the triploid bush growth habit of the plant.

The triploid bush hybrid has, due to the presence of the recessive bush allele "b" (and the absence of the dominant B allele), a longest vine length of not longer than about 150 cm, preferably not longer than about 140 cm, more preferably not longer than about 100 cm, whereby the average plant diameter is about 300 cm or less, 280 cm or less, or 200 cm or less, and an average internode length on the longest vine of about 7 cm or less, but at least about 4.7 cm, preferably at least about 5.0, 5.5, 6.0, 6.5 or 7.0 cm. Especially plants having an average internode length of 6.0 cm or 7.0 cm, or of 6.0 to 7.0 cm, are encompassed. The recessive bush allele does not affect leaf size, so that the plant according to the invention comprises leaves of similar (average) size as found in normal growth type triploid hybrids (such as Boston F1), i.e. of at least about 11, 12, 13, 14 or 15 cm long and/or at least about 15 cm wide, encompassing average leaf lengths of at least about 11, 12, 13, 14, 15, 16 or 17 cm and/or average leaf widths of at least about 15, 16, 17, 18 or 19 cm. In one embodiment the product of average leaf length multiplied by average leaf width is preferably at least about 140 or 150, such as at least about 160, 170, 180, 190 or 200, or even at least about 225, 250, 300 or more.

In one embodiment the ratio of the (average) longest vine length to the (average) number of internodes on the longest vine is 7 or less. In another aspect the triploid bush hybrid has not more than (on average) 15 internodes on the longest vine. Especially, the number of internodes on the longest vine is about 50% of the number found in Boston F1 or Fashion F1.

Also the (average) stem diameter, measured in the middle of the longest vine, is bigger than in normal triploid hybrids such as Boston F1, e.g. the average stem diameter is at least about 8 mm, preferably at least about 9 mm and may even be at least about 10 mm, 11 mm or 12 mm. The average stem diameter of a triploid bush hybrid according to the invention is thus preferably at least 1.2 times, 1.3 times, 1.4 times 1.5 times or 1.6 times the average stem diameter of a non-bush (normal growth type) triploid hybrid, comprising the B allele.

Figure 2:
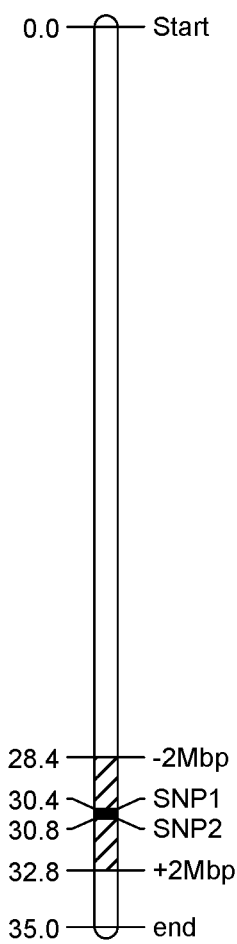

It was found that the recessive bush allele is located on chromosome 9, in the region starting at 28 Mb and ending at 33 Mb of chromosome 9, especially in the region starting at 28 Mb and ending at 32 Mb, or starting at 29 Mb and ending at 32 Mb, or starting at 29 Mb and ending at 33 Mb of chromosome 9, see also FIG. 2. Two SNP markers, which are physically linked to the recessive bush allele were identified. SNP1 is located at position 30.382.688 and has a 'T' nucleotide at that position if the bush allele is present and a 'C' nucleotide at that position when the B allele is present. SNP1, thus, comprises a 'T' at nucleotide 76 of SEQ ID NO: 1, or at the equivalent nucleotide of a sequence comprising at least 90%, 91%, 92%, 93%, 94%, 95%, 96%, 97% or more sequence identity to SEQ ID NO:1. SNP2, thus, comprises a 'A' at nucleotide 76 of SEQ ID NO: 2, or at the equivalent nucleotide of a sequence comprising at least 90%, 91%, 92%, 93%, 94%, 95%, 96%, 97% or more sequence identity to SEQ ID NO:2.

Other molecular markers which are within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which are physically linked to the bush allele can now also be identified by the skilled person, for example by sequencing the genomic region located either side of SNP1 or SNP2. As the bush allele was mapped to be within a distance of equal to or less than 1 Mb from SNP1, such other molecular markers may also be markers within the bush allele itself.

Using these markers watermelon plants, plant parts, seeds or DNA from such plants, plant parts or seeds can be screened for the presence of the recessive bush allele in the genome, in one or more copies, by genotyping for these markers. Genotyping can replace phenotyping or can be used in addition to phenotyping in any of the methods described herein, including breeding methods.

In one aspect a method for identifying, and optionally selecting, a watermelon plant or plant part or seed or genomic DNA of any of these, comprising one or more copies of the bush allele is provided, said method comprising identifying a plant or plant part or seed or genomic DNA sample of any of these comprising a Thymine (T) at nucleotide 76 of SEQ ID NO: 1 or at the equivalent nucleotide of a sequence comprising at least 90%, 91%, 92%, 93%, 94%, 95%, 96%, 97% or more sequence identity to SEQ ID NO:1; and/or a adenine (A) at nucleotide 76 of SEQ ID NO: 2 or at the equivalent nucleotide of a sequence comprising at least 90%, 91%, 92%, 93%, 94%, 95%, 96%, 97% or more sequence identity to SEQ ID NO:2; and/or any other molecular marker which is within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which is physically linked to the bush allele.

The watermelon plant or plant part or seed or genomic DNA sample may be from a diploid, tetraploid or triploid watermelon plant or plant part or seed or genomic DNA of any of these.

So in one aspect the watermelon plant or plant part or seed or genomic DNA sample is from a diploid watermelon plant, which comprises one or two copies of bush allele and whereby the presence of the bush allele is identified by the presence of one or two Thymines (T) at nucleotide 76 of SEQ ID NO: 1 or at the equivalent nucleotide of a sequence comprising at least 90%, 91%, 92%, 93%, 94%, 95%, 96%, 97% or more sequence identity to SEQ ID NO:1; and/or the presence of one or two adenines (A) at nucleotide 76 of SEQ ID NO: 2 or at the equivalent nucleotide of a sequence comprising at least 90%, 91%, 92%, 93%, 94%, 95%, 96%, 97% or more sequence identity to SEQ ID NO:2; and/or the presence of one or two copies of any other molecular marker which is within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which is physically linked to the bush allele.

If the bush allele is in homozygous form, the SNP1 genotype is TT and/or the SNP2 genotype is AA and/or the genotype of the other molecular marker is homozygous.

So in another aspect the watermelon plant or plant part or seed or genomic DNA sample is from a tetraploid watermelon plant, which comprises one, two, three or four copies of bush allele and whereby the presence of the bush allele is identified by the presence of one, two, three or four Thymines (T) at nucleotide 76 of SEQ ID NO: 1 or at the equivalent nucleotide of a sequence comprising at least 90%, 91%, 92%, 93%, 94%, 95%, 96%, 97% or more sequence identity to SEQ ID NO:1; and/or the presence of one, two, three or four adenines (A) at nucleotide 76 of SEQ ID NO: 2 or at the equivalent nucleotide of a sequence comprising at least 90%, 91%, 92%, 93%, 94%, 95%, 96%, 97% or more sequence identity to SEQ ID NO:2; and/or the presence of one, two, three or four copies of any other molecular marker which is within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which is physically linked to the bush allele. If the bush allele is in tetraploid form, the SNP1 genotype is TTTT and/or the SNP2 genotype is AAAA and/or the genotype of the other molecular marker is tetraploid.

In another aspect the watermelon plant or plant part or seed or genomic DNA sample is from a triploid watermelon plant, which comprises one, two or three copies of bush allele and whereby the presence of the bush allele is identified by the presence of one, two or three Thymines (T) at nucleotide 76 of SEQ ID NO: 1 or at the equivalent nucleotide of a sequence comprising at least 90%, 91%, 92%, 93%, 94%, 95%, 96%, 97% or more sequence identity to SEQ ID NO:1; and/or the presence of one, two or three adenines (A) at nucleotide 76 of SEQ ID NO: 2 or at the equivalent nucleotide of a sequence comprising at least 90%, 91%, 92%, 93%, 94%, 95%, 96%, 97% or more sequence identity to SEQ ID NO:2; and/or the presence of one, two or three copies of any other molecular marker which is within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which is physically linked to the bush allele. If the bush allele is in triploid form, the SNP1 genotype is TTT and/or the SNP2 genotype is AAA and/or the genotype of the other molecular marker is triploid.

The above marker genotyping may be used for selecting a watermelon plant, plant part or seed comprising one, two, three or four copies of the recessive bush allele.

In a further aspect a method for screening, and optionally selecting, watermelon seeds, plants or plant parts or DNA from such seeds, plants or plant parts for the presence of one or more markers linked to the recessive bush allele on chromosome 9 is provided, said method comprising determining the presence of:
  a) a Thymine (T) at nucleotide 76 of SEQ ID NO: 1 (SNP1) or of a sequence comprising at least 90%, 91%, 92%, 93%, 94%, 95%, 96%, 97%, 98% or 99% sequence identity to SEQ ID NO: 1; and/or
  b) a Adenine (A) at nucleotide 76 of SEQ ID NO: 2 (SNP2) or of a sequence comprising at least 90%, 91%, 92%, 93%, 94%, 95%, 96%, 97%, 98% or 99% sequence identity to SEQ ID NO: 2; and/or c) a molecular marker within 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which is physically linked to the bush allele.

Again, the watermelon plant or plant part or seed or genomic DNA sample may be from a diploid, tetraploid or triploid watermelon plant or plant part or seed or genomic DNA of any of these.

The method may further comprise selecting a watermelon plant or plant part or seed comprising one, two, three or four copies of the recessive bush allele. Thus, if two copies are present, two copies of SNP1 and/or SNP2 and/or the molecular marker of step c) are present, if three copies are present three copies of SNP1 and/or SNP2 and/or the molecular marker of step c) are present and if four copies are present, four copies of SNP1 and/or SNP2 and/or the molecular marker of step c) are present and detected (and optionally seeds, plants or plant parts are selected).

Also a method of breeding a watermelon line or variety comprising a bush growth habit is provided, whereby said method comprising in at least one step of the breeding program a marker genotyping step as described above, i.e. a step wherein the presence of SNP1, SNP2 or another marker linked to the bush allele is determined.

In another aspect a method of determining the copy number of the recessive bush allele in a watermelon plant or plant part or seed or genomic DNA of any of these is provided, said method comprising genotyping said plant or plant part or seed or genomic DNA sample of any of these for the presence of one, two, three or four Thymines (T) at nucleotide 76 of SEQ ID NO: 1 or at the equivalent nucleotide of a sequence comprising at least 90%, 91%, 92%, 93%, 94%, 95%, 96%, 97% or more sequence identity to SEQ ID NO:1; and/or for the presence of one, two, three or four adenines (A) at nucleotide 76 of SEQ ID NO: 2 or at the equivalent nucleotide of a sequence comprising at least 90%, 91%, 92%, 93%, 94%, 95%, 96%, 97% or more sequence identity to SEQ ID NO:2; and/or for the presence of one, two, three or four copies of another molecular marker which is within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which is physically linked to the bush allele.

The molecular markers described herein may be detected according to standard method. For example SNP markers can easily be detected using a KASP-assay (see world wide web at kpbioscience.co.uk) or other SNP genotyping assays. For developing a KASP-assay, for example 70 base pairs upstream and 70 base pairs downstream of the SNP can be selected and two allele-specific forward primers and one allele specific reverse primer can be designed. See e.g. Allen et al. 2011, Plant Biotechnology J. 9, 1086-1099, especially p 097-1098 for KASP assay method.

Thus, in one aspect, the SNP markers and the presence/absence of the marker associated with the bush allele is determined using a KASP assay, but equally other genotyping assays can be used. For example, a TaqMan SNP genotyping assay, a High Resolution Melting (HRM) assay, SNP-genotyping arrays (e.g. Fluidigm, Illumina, etc.) or DNA sequencing may equally be used.

Genotyping of diploid plants or plant parts (cells, leaves, DNA, etc.) can distinguish SNP genotypes, e.g. plants or parts comprising TT for SNP1 can be distinguished from plants or parts comprising TA for SNP1 in their genome.

Genotyping of tetraploid plants or plant parts (cells, leaves, DNA, etc.) can be done in the same way as for diploids, using for example a KASP-assay to distinguish SNP genotypes, e.g. plants or parts comprising TTTT for SNP1 can be distinguished from plants or parts comprising TTTA, TTAA, TAAA or AAAA for SNP1 in their genome.

The same applies for triploids. Thus, genotyping of triploid plants or plant parts (cells, leaves, DNA, etc.) can be done in the same way, using for example a KASP-assay to distinguish SNP genotypes, e.g. plants or parts comprising TTT for SNP1 can be distinguished from plants or parts comprising TTA, TAA, AAA for SNP1 in their genome.

The recessive bush allele can be transferred into any other watermelon plant, by e.g. making crosses with plants grown from the deposited seeds, or by regenerating plants from tissue or cell cultures of the plants for which seeds have been deposited and making crosses with such regenerated plants, or by identifying diploid watermelon plants comprising the bush allele (e.g. plants which may not show the bush-growth type because they also contain the B allele). The other watermelon plants into which the b allele can be transferred are thus, for example, plants which lack the recessive b allele. Thus, to transfer the bush allele, a watermelon plant comprising the bush allele is crossed with another watermelon plant e.g. lacking the b allele and the F1 is selfed to produce an F2 or further generation. The F2 or further generation progeny which contain the bush allele in homozygous form in diploids (or in three or four copies in triploids or tetraploids) will show the bush growth habit and can thus easily be identified.

In order to test whether another watermelon plant has a bush allele or not, a marker assay can be done as described herein.

To determine and/or select plant lines having the bush growth characteristics as described above (for example when transferring the bush allele into other watermelon plants lacking the recessive bush allele), it is understood that several plants of a line are grown in one or more locations under the same environmental conditions, including appropriate control varieties or lines, and measurements are done on a plurality of plants of a line (at least 3, preferably at least 5 or 10 or more plants) in order to be able to calculate a mean value. As mentioned before, phenotyping for the bush growth habit can be replaced by genotyping (or genotyping can be used in addition to phenotyping), i.e. by determining the presence of one or more of the markers linked to the bush allele on chromosome 9.

Thus, in one aspect the use of SNP1, SNP2 and/or molecular marker which is within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 for breeding a watermelon plant comprising one or more bush alleles or for identifying a watermelon plant or plant part or seed or DNA comprising one or more bush alleles is provided herein.

Also a kit for detecting the presence of one or more bush alleles in a plant, seed, plant part or genomic DNA, said kit comprising DNA primers which can detect the presence of a Thymines (T) at nucleotide 76 of SEQ ID NO: 1 or at the equivalent nucleotide of a sequence comprising at least 90%, 91%, 92%, 93%, 94%, 95%, 96%, 97% or more sequence identity to SEQ ID NO:1; and/or the presence of an adenine (A) at nucleotide 76 of SEQ ID NO: 2 or at the equivalent nucleotide of a sequence comprising at least 90%, 91%, 92%, 93%, 94%, 95%, 96%, 97% or more sequence identity to SEQ ID NO:2; and/or the presence of another molecular marker which is within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which is physically linked to the bush allele.

The kit may for example be a kit for performing a SNP assay for detecting any of the markers linked to the bush allele, e.g. a KASP assay or Taqman assay. A KASP assay for example comprises three DNA primers, see Examples, which detect the presence of SNP1 or SNP2 or another marker.

Fruit characteristics are not influenced by the presence of three copies of the bush allele (absence of the B allele), so that triploid hybrids with any size of fruit, any fruit shape, color and fruit rind pattern can be produced by crossing the bush allele into genetic backgrounds which have different fruit characteristics. The bush allele can, for example, be backcrossed into different genetic backgrounds by using seed deposited herein as a source of the bush allele, as described elsewhere herein. Alternatively, genes determining different fruit characteristics can be backcrossed into plants comprising the bush growth type. Thus, average fruit weight of a triploid hybrid comprising the bush growth type may be at least about 5, 6, 7, 8, 9, 10, 11, 12, 13 or 14 kg. In another embodiment average fruit weight of a triploid hybrid comprising the bush growth type may be less than 5 kg, e.g. 4, 3, 2, 1.5 or 1 kg. For producing hybrid triploids with such small fruits one can for example introduce the bush allele into varieties such as Liliput, Extazy or Fantazy (Hazera) or Valdoria F1, Vanessa F1, Pixie F1 or Bonny F1 (Nunhems) or, vice versa, genes determining small fruit size can be backcrossed into plants deposited herein, having a bush growth type.

Likewise, any other fruit characteristics may be combined with the bush growth type by breeding. As mentioned, for example fruit shape (e.g. elongate, oval, blocky, spherical or round), fruit surface (furrow, smooth), flesh color (scarlet red, coral red, orange, salmon, yellow, canary yellow or white), rind color (e.g. light green; dark green; green-striped with narrow, medium or wide stripes; grey types; with or without spotting; Golden yellow), rind thickness, rind toughness, rind pattern (e.g. striped, non-striped, netted), brix (total soluble solids), flesh structure/flesh firmness, higher lycopene and/or vitamin content, different sugar: acid ratios, very good fruit flavour, etc. may be modified by breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar:acid ratio, good flavor, high vitamin and lycopene content, firm flesh texture, non-fibrous flesh texture, freedom from defects such as hollow heart, rind necrosis, blossom-end rot or cross stitch and good rind characteristics and cracking-resistance).

In one embodiment of the invention, the fruits preferably also do not have a "brittle rind" and/or an "explosive rind" as described in WO03/075641 on page 13 and 14, i.e. the fruits do not break under pressure in the range of 90 to 140 g/mm².

The bush allele can be introduced into other watermelon plants lacking the bush allele using known breeding methods. Known breeding methods can be used alone or in combination, such as (but not limited to) recurrent selection, pedigree breeding, backcross breeding, inbred development, hybrid testing, marker assisted breeding, etc. Progeny are then selected which retain the bush growth habit, which can be easily identified phenotypically. Thus, selection of progeny plants having the bush growth habit can be done by phenotypic selection of the bush growth habit characteristics and by discarding plants which do not have the bush growth habit characteristics, e.g. which have longer main vines, longer internodes and smaller leaves compared to a bush plant according to the invention.

Alternatively or in addition progeny plants can be selected for the presence of the bush genotype of SNP1 and/or SNP2, and optionally any other molecular marker which is indicative of the presence of the bush allele and is physically linked to SNP1 or SNP2 within 2 Mb, 1.5 Mb, 1 Mb, or less, either side of SNP1 or SNP2.

Thus, in one aspect a plant of the species *Citrullus lanatus* is provided, wherein said plant is triploid and has a bush growth habit, and comprises three copies of a recessive allele designated bush, wherein the bush allele is obtainable by (can be obtained by) crossing a watermelon plant of which seeds were deposited under Accession number NCIMB41906 or NCIMB41905, or progeny of any of these plants (e.g. obtained by selfing and/or crossing and which progeny retain the bush allele and/or the bush growth habit), with another watermelon plant.

In one aspect, the triploid plant having a bush growth habit is obtainable by crossing a diploid bush watermelon plant with a tetraploid bush watermelon plant, wherein the bush allele is obtainable by (can be obtained by) crossing a watermelon plant of which seeds were deposited under Accession number NCIMB41906 or NCIMB41905, or progeny of any of these plants (e.g. obtained by selfing and/or crossing and which progeny retain the bush allele and/or the bush growth habit), with another watermelon plant.

In one aspect a plant of the species *Citrullus lanatus* is provided, wherein said plant is triploid and has a bush growth habit, and comprises three copies of a recessive allele designated bush, wherein the plant is obtainable by (can be obtained by) vegetative propagation of plant cells or plant tissue of a watermelon plant of which seeds were deposited under Accession number NCIMB 41907.

As the b allele is recessive, the bush growth habit is only seen if no dominant B allele is present. When transferring the b allele from a diploid seed deposit made herein (e.g. NCIMB 41906 or progeny thereof) to another watermelon plant which does not contain the recessive b allele, the F1 will be heterozygous and will not display the bush growth habit and the breeder first needs to self the F1 to identify plants comprising the bush growth habit. Likewise, when transferring the b allele from a tetraploid watermelon plant (bbbb), such as grown from seeds of NCIMB41905 or progeny thereof, to another tetraploid watermelon plant not comprising the recessive b allele, the F1 will be heterozygous and not display the bush growth habit and again the bush phenotype will only be seen in the F2 generation. A diploid bush plant can also be regenerated from the haploid cells of a tetraploid bush plant (e.g. pollen or anther culture and regeneration of a plant) and the derived diploid bush plant may then be used in further breeding and in generating watermelon plants having a bush growth habit. This may be referred to as a haploid tetraploid plant having a bush growth habit. Such plants are encompassed herein.

Alternatively, the molecular markers provided herein, such as SNP1 and/or SNP2, can be used to determine whether the bush allele is present or absent in any plant, plant part, plant cell or progeny or parent, without the need for phenotypic testing. Thus, in one embodiment the b allele can be introduced into other watermelon plants lacking the b allele by marker assisted breeding methods, using SNP1 and/or SNP2 or another molecular marker linked to the b allele, e.g. within 2 Mb, 1.5 Mb, 1 Mb or less of SNP1 and/or SNP2.

A diploid watermelon plant with a bush growth habit, or plant part, comprises two copies of the b allele and also two copies of the marker genotype linked to the b allele, so for SNP1 the genotype is TT and/or for SNP2 the genotype is AA. Similarly a tetraploid plant with a bush growth habit, or plant part, comprises four copies of the b allele and also four copies of the marker genotype linked to the b allele, so for SNP1 the genotype is TTTT and/or for SNP2 the genotype is AAAA. Likewise a triploid plant with a bush growth habit, or plant part, comprises three copies the b allele and also three copies of the marker genotype linked to the b allele, so for SNP1 the genotype is TTT and/or for SNP2 the genotype is AAA.

Alternatively, other molecular markers may be developed which are linked to the b allele and then selection of the bush growth habit may be done by selecting for plants having the linked molecular markers. Linked markers can be developed using a range of techniques, such as Bulk Segregant Analysis, and a range of markers, such as AFLP markers, RFLP markers, SNP markers, mini- or micro-satellite markers, etc. For marker development a segregating population should be generated by e.g. crossing a plant having a bush growth type (e.g. a diploid bb) with a plant having a normal growth type (e.g. a diploid BB) and developing segregating population therefrom (e.g. an F2 or F3 population or backcross population). Markers can then be identified which are closely associated (linked) with the bush growth habit and the bush allele, i.e. co-segregates with the b allele. See for example Wolukau et al. (HortScience February 2009 vol. 44 no. 1 32-34) the use of Bulk Segregant Analysis in melon to identify markers linked to a resistance gene. A molecular marker is a DNA sequence or single nucleotide polymorphism (SNP) which is found on the chromosome close to the b allele (e.g. within a genetic distance of 5 cM or less) and which is different from the DNA sequence or SNP found close to the B allele. Thus, in one embodiment the b allele can be introduced into other watermelon plants lacking the b allele by marker assisted breeding methods, using a molecular marker closely linked to the b allele, such as SNP1, SNP2 or any marker within 2 Mb, 1.5 Mb, 1 Mb or less from SNP1 or SNP2 and which markers is physically linked to the b allele.

For seedless fruit production, the triploid bush hybrid according to the invention may be interplanted with a suitable diploid pollenizer, such as for example Jenny F1 (Nunhems) or Polimax F1 (Nunhems) or other pollenizers, such as SP-1, SP-2, SP-3, SP-4 or SP-5 (Syngenta) or Sidekick. Fruit are then harvested from the triploid plants of the invention. As the triploid plants have a smaller plant diameter, a higher seeding or planting density is possible compared to normal growth type triploids (such as plants having a main vine length of above 200, 250, or 300 cm). Thereby also a higher triploid fruit yield per hectare is achieved.

In one embodiment a method for producing seedless triploid fruits is provided, comprising:
 a) interplanting triploid hybrid bush plants and diploid pollenizer plants, wherein the triploid plants are at a density which is at least 1.5 times the planting density of a normal growth type triploid hybrid plants,
 b) allowing pollination of the female flowers on the triploid bush plants to occur, and
 c) harvesting the fruits from the triploid hybrid bush plants.

The density of the triploid bush plants in step a) depends on whether or not the plants are grown in the greenhouse or in the open field and whether or not the triploids are grafted onto rootstocks or not. Thus, the density of triploid bush plants in the greenhouse is preferably at least about 7500 plants per hectare (grafted triploids) or 15000 plants per hectare (non-grafted triploids). The density of triploid bush plants in the open field is preferably at least about 6000, 7000 or 8000 plants per hectare (grafted triploids) or at least about 12000, 13000, 14000 or 15000 plants per hectare (non-grafted triploids).

The triploid fruit yield in step c) is at least 1.25 times the triploid fruit yield of normal growth type triploids, such as Boston F1 or Fashion F1. Thus in the open field (non-grafted) at least about 75 tonnes triploid seedless fruits (comprising three copies of the b allele) per hectare is harvested in step c), preferably even at least about 80, 85 or 90 tonnes per hectare. Thus in one embodiment the method comprises step d) harvesting at least 75 tonnes per hectare triploid fruits. These can then be sorted, packaged in containers etc. Containers comprising or consisting of triploid fruits, preferably marketable fruits, comprising the b allele are also an embodiment of the invention.

Also seeds from which triploid hybrid plants having a bush growth type can be grown are provided herein. Thus, in one embodiment a watermelon seed is provided from which a triploid bush plant as described above can be grown. The seed contains three copies of the b allele and three copies of SNP1 and/or SNP2 and/or any other marker linked to the recessive bush allele. In one embodiment a representative sample of seeds has been deposited under Accession number NCIMB 41907. In one embodiment the mature seeds are small, comprising an average seed size of equal to or less than 5 mm length. Packages (bags, containers, etc.) comprising a plurality of such seeds are encompassed herein.

Also seedlings, scions and rootstocks, as well as cells and tissues, and cell cultures and tissue cultures, and vegetative propagations of the triploid hybrid plants having a bush growth type are encompassed herein. Thus whole plants obtained from seedlings, scions and rootstocks, as well as cells and tissues, cell cultures and tissue cultures and vegetative propagations of the triploid hybrid plants retaining the bush growth type according to the invention when regenerated into a plant and grown under the same environmental conditions are provided herein.

Likewise seedless triploid fruit (bbb) harvested from a triploid bush plant according to the invention are encompassed herein. The fruits may be harvested for fresh consumption or for processing. Containers comprising or consisting of a plurality of such fruits are a further embodiment of the invention. Preferably the containers comprise marketable fruits.

The triploid hybrid plant having a bush growth type (bbb) is an F1-hybrid produced from a cross between a diploid inbred male parent line, which has a bush growth habit, and a tetraploid inbred parent line, which has a bush growth habit (see FIG. 1). Thus, to produce seeds of triploid hybrid plants having a bush growth type (bbb) one can either vegetatively propagate the triploid hybrid plant or, alternatively, one can produce inbred bush diploid (bb) and inbred tetraploid bush (bbbb) parent lines. The skilled person can, thus, introduce different characteristics (such as various fruit sizes etc.) into a triploid bush hybrid by first generating male and female parents having different characteristics, but retaining the bush growth type as described herein.

A vegetatively propagated triploid hybrid having a bush growth habit is also an embodiment of the invention. In one aspect, the watermelon plant has the bush allele as found in seeds deposited under NCIMB41907, NCIMB41906 or NCIMB41905. In one aspect the vegetatively propagated hybrid is obtained from (obtainable from) plant tissue of NCIMB 41907.

As mentioned above, the b allele can be transferred from seed deposits provided herein into other watermelon plants and thereby other inbred bush diploids and/or other inbred bush tetraploids can be made. In one embodiment an inbred diploid bush plant and/or an inbred tetraploid bush plant comprising the b allele as found in seeds deposited under Accession numbers NCIMB 41905, NCIMB 41906 and/or NCIMB 41907 is provided.

When referring to a diploid or tetraploid watermelon plant having a bush growth habit, it is understood that the same bush growth habit characteristics as described above for the triploid bush hybrid are referred to, i.e. the diploid or tetraploid bush plant has, due to the presence of the recessive bush allele "b" in two or four copies (and the absence of the dominant B allele), a longest vine length of no longer than about 150 cm, 140 cm, or 100 cm, whereby the average plant diameter is about 300 cm, 280 cm or 200 cm or less and an average internode length on the longest vine of about 7 cm or less, but at least about 4.7 cm, preferably at least about 5.0, 5.5, 6.0 or 6.5 cm. The recessive bush allele does not affect leaf size, so that the plant according to the invention comprises leaves of similar size as found in normal growth type diploids (such as variety Milady) or normal growth type tetraploids, i.e. of at least about 11 cm long and/or at least about 15 cm wide, encompassing leaf lengths of at least about 11, 12, 13, 14, 15, 16 or 17 cm and/or leaf widths of at least about 15, 16, 17, 18 or 19 cm. Similarly, the ratio of the (average) longest vine length to the (average) number of internodes on the longest vine is 7 or less. In another aspect the diploid bush or tetraploid bush has not more than (on average) 25, 21, or 15 internodes on the longest vine. Also the (average) stem diameter, measured in the middle of the longest vine, is in one aspect bigger than in normal growth type diploids or tetraploids, e.g. the stem diameter is at least about 8 mm, preferably at least about 9 mm and may even be at least about 10 mm, 11 mm or 12 mm. The average stem diameter of a diploid or tetraploid bush plant according to the invention is, thus, preferably at least 1.2 times, 1.3 times, 1.4 times 1.5 times or 1.6 times the average stem diameter of a non-bush diploid or tetraploid, comprising the B allele. Fruit characteristics (e.g. average fruit size, weight, etc.) are in one embodiment no different than in normal growth type diploids or tetraploids.

In one embodiment a diploid bush inbred line can be made wherein the bush allele (b) is derivable e.g. from the seed deposit made under Accession number NCIMB 41906 or from progeny thereof, e.g. progeny obtained by selfing and/or crossing NCIMB41906 with another watermelon plant. This may for example be done by breeding with NCIMB 41906, or progeny thereof, and selecting in the progeny generations for the bush growth type, while discarding plants which do not have the bush growth type. The bush allele may also be derived from other plants or plant parts comprising the bush allele, e.g. pollen or ovaries of a tetraploid bush plant, such as seeds deposited under NCIMB 41905.

Alternatively, new diploid bush inbred lines can be made by identifying diploid varieties or lines which may comprise a bush allele even though they may not have a bush growth type (due to the dominant B allele being present). For example diploids which are suspected to maybe contain a b allele may be used. An allelism test can be done to determine whether a recessive bush allele is present. Preferably the diploid is self-pollinated for one or more generations and a diploid which is homozygous for the bush allele is identified by selecting progeny plants having the bush growth type as determined by the bush allele in homozygous form. Varieties which might be suitable are Garden Baby, Bush Charleston Gray and Bush Sugar Baby or Sugar Bush.

Such varieties may be genotyped for the presence of the bush allele using one or more of the markers provided herein, so e.g. SNP1 and/or SNP2 or any marker within a physical distance 2 Mb, 1.5 Mb, 1 Mb or less of any one of these markers.

In one embodiment a tetraploid bush inbred line can be made wherein the bush allele is derivable e.g. from the seed deposit made under Accession number NCIMB 41905 or NCIMB 41906, or from progeny of any of these. This may, for example, be done by breeding with NCIMB 41905 and/or NCIMB 41906, or progeny of these, and selecting in the progeny generations for the bush growth type and/or for one or more of the markers linked to the b allele, while discarding plants which do not have the bush growth type and/or which do not have the SNP genotype or molecular marker genotype or haplotype indicative of the presence of the bush allele. When NCIMB 41906, or progeny thereof, is/are used, chromosome doubling techniques may be used to generate tetraploids, followed by selection of the bush growth habit in the tetraploids and/or the bush SNP genotype or other molecular marker linked to the bush allele (as described elsewhere) and in progeny of the tetraploids obtained by selfing selected tetraploids and stabilization of the bush growth habit in further generations.

Alternatively, new tetraploid bush inbred lines can be made starting from new diploid bush plants as described above and inbreeding said plants for several generations, while selecting for the bush growth type and/or the bush SNP genotype or other molecular marker linked to the bush allele (as described elsewhere) as defined herein, and doubling the chromosome of a select inbred bush diploid line to generate a tetraploid bush line. The tetraploid line is then inbred further for several generations, selecting for the bush growth type and/or the bush SNP genotype or other molecular marker linked to the bush allele (as described elsewhere) as described herein.

In one aspect, the invention also provides a plant (or seed) of the species *Citrullus lanatus* wherein said plant is tetraploid and has a bush growth habit. The bush growth habit is due to the presence of the b allele, thus a tetraploid plant having a bush growth habit and comprising four copies of a recessive allele designated bush is provided, wherein a representative sample of seed containing said b allele has been deposited under accession number NCIMB 41905. Also any plant parts and progeny of a tetraploid bush plant, such as vegetative propagations, seed propagations (e.g. selfings) and also in vitro cell- or tissue cultures, as well as pollen, ovaries, etc. are encompassed herein. Thus, in one embodiment the tetraploid bush plant, or seeds from which the plant can be grown, or tissue or parts of the plant (pollen, anthers, ovules) comprises the b allele as found in NCIMB 41905.

Thus, in one aspect a plant of the species *Citrullus lanatus* is provided, wherein said plant is tetraploid and has a bush growth habit, and comprises four copies of a recessive allele designated bush, wherein the bush allele is obtainable by (can be obtained by) crossing a watermelon plant of which seeds were deposited under Accession number NCIMB41906 or NCIMB41905, or progeny of any of these plants (e.g. obtained by selfing and/or crossing), with another watermelon plant.

In another aspect a plant of the species *Citrullus lanatus* is provided, wherein said plant is tetraploid and has a bush growth habit, and comprises four copies of a recessive allele designated bush, wherein the plant is obtained by selfing a tetraploid plant of which a representative sample of seeds was deposited under Accession number NCIMB 41905.

Likewise a plant or seed or a plant part of the species *Citrullus lanatus* wherein said plant is tetraploid and has a bush growth habit due to the presence of four copies of a recessive allele designated bush on chromosome 9 is provided, which allele is detectable by a thymine (T) at nucleotide 76 of SEQ ID NO: 1 or at the equivalent nucleotide of a sequence comprising at least 90%, 91%, 92%, 93%, 94%, 95%, 96%, 97% or more sequence identity to SEQ ID NO:1; and/or a adenine (A) at nucleotide 76 of SEQ ID NO: 2 or at the equivalent nucleotide of a sequence comprising at least 90%, 91%, 92%, 93%, 94%, 95%, 96%, 97% or more sequence identity to SEQ ID NO:2; and/or any other molecular marker which is within a physical distance of 2 Mb, 1.5 Mb, 1 Mb, 0.8 Mb, 0.6 Mb, 0.4 Mb, 0.3 Mb, 0.2 Mb, 0.1 Mb, 90 kb, 80 kb, 70 kb, 60 kb, 50 kb, 30 kb, 20 kb, 10 kb, 5 kb, 2 kb, 1 kb or less of SNP1 or SNP2 and which is physically linked to the bush allele.

A vegetatively propagated tetraploid watermelon plant having a bush growth habit is also an embodiment of the invention. In one aspect, the watermelon plant has the bush allele as found in seeds deposited under NCIMB41907, NCIMB41906 or NCIMB41905. In one aspect the vegetatively propagated watermelon plant is obtained from (obtainable from) plant cells or plant tissue of NCIMB 41905.

In one aspect a plant of the species *Citrullus lanatus* is provided, wherein said plant is tetraploid and has a bush growth habit, and comprises four copies of a recessive allele designated bush, wherein the plant is obtainable by (can be obtained by) vegetative propagation of plant cells or tissue of a watermelon plant of which seeds were deposited under Accession number NCIMB41905.

In another embodiment the tetraploid bush plant comprises a b allele identified from other diploid sources as described above or as found in seeds deposited under accession number NCIMB 41906.

A method for generating a tetraploid inbred plant having a bush growth type is provided, comprising the steps of:
a) providing a diploid plant comprising the b allele,
b) selfing said diploid plant for several generations to generate an inbred line having a bush growth type,
c) doubling the chromosomes of said inbred line to generate a tetraploid line,
d) selfing the tetraploid line for several generations.

Thus, in step a) the diploid plant may be a plant derived from seed deposited under NCIMB 41906 or progeny thereof, or may be a diploid plant into which the b allele from seed deposit NCIMB 41906 has been transferred by crossing and selection of the bush growth type. The diploid may also be new diploid plant in which the b allele has been identified e.g. by using an allelism test and/or by identifying a diploid which may comprise the b allele, selfing said plant for one or more generations and selecting a progeny plant phenotypically having the bush growth type. Alternatively the diploid may be a haploid plant generated from seed deposited under NCIMB 41905.

Also the use of the tetraploid bush plant according to the invention as male or female parent is provided, whereby the tetraploid bush plant is crossed with another watermelon plant or is allowed to self-fertilize to produce progeny. In one embodiment the tetraploid bush plant comprises a bush growth type, due to the presence of four copies of the b allele, wherein the bush plant (and/or the b allele) is obtainable from seeds deposited under NCIMB 41905, or progeny thereof.

Further the use of the tetraploid bush plant as female parent is provided, especially as a female parent in hybrid triploid watermelon seed production (i.e. F1 seed production). Thus, in one aspect the female flowers of the tetraploid bush plant are pollinated (or allowed to be pollinated) with pollen of another watermelon plant. The other watermelon plant may be any watermelon plant, e.g. a diploid or a tetraploid watermelon plant. In a specific embodiment the other watermelon plant is a diploid plant, preferably a diploid plant comprising a bush growth type. The diploid watermelon plant comprising a bush growth type may be any diploid bush plant as described above, or a plant obtainable from seed deposited under NCIMB 41906, or progeny thereof.

Also provided is a method for producing triploid hybrid watermelon seeds, wherein triploid plants grown from such seeds have a bush growth habit, said method comprising:
(a) providing a diploid watermelon plant having a bush growth habit and a tetraploid plant having a bush growth habit,
(b) allowing pollination of pistillate flowers of the tetraploid bush plant with pollen of the diploid bush plant, and
(c) harvesting seeds produced in the fruits of the tetraploid bush plant, and optionally
(d) drying the harvested seeds.

Optionally the dried and harvested F1 seeds are then packaged. They may also be treated prior to packaging. Thus packages or containers comprising or consisting of seeds obtained by the above method are an embodiment herein.

This method is also illustrated in FIG. 1. The tetraploid bush plant and the diploid bush plant can be provided as described elsewhere herein. They may be interplanted to allow pollination to occur. In step a) seeds or seedlings of both plants are, therefore, planted and grown in proximity of each other. If the diploid bush plant and tetraploid bush plant do not flower at the same time, the plant which flowers later can be planted or sown earlier, so that flowering is at about the same time. As both the diploid plants and tetraploid plants have a bush growth habit, more plants per hectare can be seeded or planted compared to triploid hybrid seed production involving normal growth type tetraploids.

Pollination may be by hand or by insects (e.g. bees) in isolation blocks. To ensure pollination of the tetraploid female flowers with pollen from the male diploid, different methods can be used, such as collecting male flowers by hand and hand-pollinating female flowers, followed by covering the pollinated flower. Alternatively, all male (staminate) flowers that develop on the tetraploid plants may be removed to ensure pollination of the pistillate flowers on the tertaploid bush plants with diploid pollen of the diploid bush plants. When the fruits on the tetraploid plants are mature, they are harvested and the triploid F1 hybrid seeds (resulting from cross-pollination) are collected. These may then be sorted (e.g. by size), dried, optionally treated, and packaged for sale. In one embodiment the tetraploid bush female parent (and/or the b allele) is obtainable from seeds deposited under NCIMB 41905 or progeny or vegetative propagations thereof. In another embodiment the diploid bush male parent (and/or the b allele) is obtainable from seeds deposited under NCIMB 41906 or progeny or vegetative propagations thereof.

Provided are, therefore, also seeds obtained by the above method, i.e. seeds of F1-hybrids which, when grown, produce triploid plants having a bush growth habit. Such seeds may be packaged in bags, containers and the like.

In one embodiment the F1 seeds are seeds of WH3451, a representative sample of seeds have been deposited under accession number NCIMB 41907. In another embodiment the triploid bush hybrid (and/or the b allele) is obtainable from seeds deposited under NCIMB 41907 or progeny thereof or vegetative propagations thereof.

The tetraploid bush plant used in the above method comprises four copies of the bush allele (bbbb) in its genome and has the following characteristics: a longest vine length of not more than 150 cm, preferably not more than 140 cm, 135 cm, or not more than 100 cm, an average internode length on the longest vine of 7 cm or less but at least 4.5 cm, and produces leaves of at least 11 cm long and/or at least 15 cm wide.

Also provided is a method for producing tetraploid bush watermelon seed is provided, comprising a) growing a tetraploid bush watermelon plant according to the present invention, b) allowing self-pollination of said tetraploid watermelon plant, c) obtaining a fruit from a plant of step b) and d) extracting tetraploid seed from said fruit. Preferably the method further comprises washing and drying said seed. In one embodiment the tetraploid watermelon plant of step a) is a plant comprising a bush growth type as described herein. The plant may in one embodiment comprise a bush allele obtainable from seed deposited under accession numbers NCIMB 41905, NCIMB 41906 or NCIMB 41907. The plant of step a) may be obtainable from a plant, or from a plant part, grown from deposit number NCIMB 41905.

As also described further above, it is an embodiment to provide a method for seedless triploid watermelon fruit production, said method comprising:
1. providing a triploid hybrid (F1) watermelon plant comprising a bush growth habit,
2. interplanting said triploid hybrid plants with diploid pollenizer plants,
3. harvesting the seedless watermelon fruits produced on the triploid plants of (a).

The triploid hybrid plant of step 1 is preferably not grafted onto a different rootstock. The method is preferably carried out in the open field.

The diploid pollenizer in step b) may be any diploid pollenizer, such as a normal growth type (non-bush) pollenizer, commercial pollenizers such as Jenny or Polimax may be used, or Super-pollenizers (SP-1, SP-2, SP-3, SP-4, SP-5), Sidekick, Escort-4, Companion or others. Optionally, the pollenizer may be a dual purpose pollenizer as described in WO2012/069539 A1. The diploid pollenizer should produce sufficient pollen at the right time of the day and for an appropriate period of time to induce fruit set in triploid hybrids. The pollenizer plants may be hybrid diploids (F1 diploids) or open pollinated (OP) pollenizers.

In this method at least 1.5 times, preferably at least 2 times, 2.5 times or 3 times as many triploid bush plants may be grown per hectare than when a triploid hybrid plant comprising a normal (non-bush) growth habit, such as Boston F1, is used. At least 15%, preferably at least 20%, 30%, 40% or 50% more marketable triploid fruits are produced per hectare than when a triploid hybrid plant comprising a normal growth habit, such as Boston F1, is used. Total seedless fruit yield harvested from the triploid bush hybrid plants is preferably at least about 75 tonnes per hectare (t/ha), preferably at least 80 t/ha, more preferably at least 90 t/ha.

Interplanting in one field may be either done by seeding or transplants of the pollenizer and triploids. Various interplanting methods can be used, as known in the art and various ratios of pollenizer:triploid hybrid may be used. One row of pollenizer plants may for example be present at at least every 2, at least every 3 or at least every 4 rows of triploids, but other methods of interplanting may also be used.

Pollination is usually done by bees, and bee hives can be provided to the fields unless sufficient wild bees are naturally present. Pollination can also be performed by manual or mechanical means. Harvest at maturity may be done by hand or mechanized.

The harvested triploid fruits may be packaged for fresh markets or for processing. Fruits comprising three b alleles obtainable by the above method are encompassed herein. These fruits can be distinguished from fruits of normal triploid hybrids in that they have the capability to produce plants having a bush growth type according to the invention, i.e. they have the genetic determinants which are responsible for the bush growth type (the b allele). If molecular markers linked to the b allele are developed as described above, marker analysis can easily distinguish such fruits. Alternatively, cells or tissues from such fruits (or from other parts of the plant from which they are harvested) can be vegetatively cultured and regenerated into whole plants, which regenerated plants have the bush growth habit. Thus, in one embodiment, harvested triploid fruits (bbb) are provided, such as packaged whole fruits or fruit parts and/or processed fruits or fruit parts.

In another aspect of the invention a cell culture or a tissue culture of regenerable cells of a plant having a bush growth habit or comprising a bush allele, all as described above, is provided. A cell culture or a tissue culture comprises cells or protoplasts or plant tissue from a plant part of a plant comprising a bush-allele (such as a bush tetraploid, bush diploid or bush triploid plant, all as described herein) selected from the group consisting of: embryos, meristems, cotyledons, pollen, leaves, anthers, roots, root tips, pistils, flowers, seed, stalk. The plant part may be selected from a scion, fruit, pollen, ovule, stem, cotyledon, leaf, cell embryos, meristems, anthers, roots, root tips, pistils, flowers, seed. Also provided is a watermelon plant regenerated from such a cell culture or tissue culture, wherein the regenerated plant (or progeny thereof, e.g. obtained after selfing) comprises a bush growth habit. Therefore, in one aspect vegetatively propagated watermelon plants obtained from plant tissue of seeds or plants grown from seeds deposited under NCIMB 41907, NCIMB 41906 or NCIMB 41905 are encompassed herein.

It is understood that it is also an object of the invention to provide seeds from which the bush diploid, triploid or tetraploid plants described herein can be grown. Also seedlings, scions and rootstocks, as well as cells and tissues of the bush diploid, triploid or tetraploid plants are encompassed herein. Such plant parts comprise the genetic determinants for producing bush plants according to the invention. Thus whole plants obtained from seedlings, scions and rootstocks, as well as from cells and tissues of the bush triploid or tetraploid plants, retain all the physiological and morphological characteristics of the bush triploid or tetraploid plants according to the invention when grown under the same environmental conditions.

Also progeny of any of the plants according to the invention are provided herein, such as seeds obtainable by crossing a plant comprising the bush allele (and lacking the B allele) described herein with another watermelon plant and/or by selfing a plant according to the invention to produce F1 seeds, and further generation progeny (F2, F3, etc.). The presence of the bush allele in the progeny can be determined by the bush growth type (e.g. in inbred lines) and/or markers analysis.

In one embodiment a tetraploid watermelon plant (and seeds from which such a plant can be grown) having a bush growth habit is provided, wherein a representative sample of seeds containing the genetic elements for said bush growth habit (i.e. containing the b allele in four copies, and not containing the B allele) is provided, wherein a representative sample of seeds has been deposited under accession number NCIMB 41905.

In one embodiment a triploid watermelon plant (and seeds from which such a plant can be grown) having a bush growth habit is provided, wherein a representative sample of seeds containing the genetic elements for said bush growth habit (i.e. containing the b allele in three copies, and not containing the B allele) is provided, wherein a representative sample of seeds has been deposited under accession number NCIMB 41907.

In one embodiment a diploid watermelon plant (and seeds from which such a plant can be grown) having a bush growth habit is provided, wherein a representative sample of seeds containing the genetic elements for said bush growth habit (i.e. containing the b allele in two copies, and not containing the B allele) is provided, wherein a representative sample of seeds has been deposited under accession number NCIMB 41906.

Watermelon seeds containing the recessive allele designated "bush" is provided, wherein a representative sample of seeds containing said "bush" allele have been deposited under accession number NCIMB 41905, NCIMB 41906 and NCIMB 41907. In one embodiment the seeds have a pedigree which includes inbred line WHAAOX or inbred line WHAAPD as one of the parental lines. Also provided is a watermelon plant produced by growing said seeds. Also pollen and ovules of the plant produced by growing said seeds is provided.

Watermelon plants obtained (derived), or obtainable (derivable), from plants according to the invention (e.g. from plants comprising a bush growth habit and/or comprising the genetic determinants, the b allele, which confers the bush growth habit) include plants obtained by breeding methods, such as selfing, crossing, backcrossing, recurrent selection, double haploid production, marker assisted selection, clonal propagations, transformants, etc., whereby the derived plants comprise a bush growth habit and/or the genetic determinants (b allele) which confers the bush growth habit (when the B allele is absent) according to the invention.

In one aspect a watermelon plant is provided, of which a representative number of seeds has been deposited under accession number NCIMB 41905, NCIMB 41906 and NCIMB 41907, or progeny of any such plants, e.g. obtained by crossing and/or selfing. In one aspect a watermelon seed is provided, of which a representative number of seeds has been deposited under accession number NCIMB 41905, NCIMB 41906 and NCIMB 41907.

Also pollen, an ovule, cells, tissues, vegetative propagations obtained from these plants, or from the progeny thereof, are provided. In one aspect progeny retain the bush allele and the bush growth habit of the plants of which seeds were deposited under NCIMB 41905, NCIMB 41906 and NCIMB 41907.

Also fruit of a watermelon plant is provided, wherein the fruit is produced by self pollination of the plant. Also triploid seedless fruit is provided, wherein the fruit is obtained by pollination of a plant grown from a watermelon plant of which a representative number of seeds have been deposited under Accession number NCIMB 41907.

Also a triploid hybrid seed obtained by crossing a diploid watermelon plant, of which a representative number of seeds have been deposited under Accession number NCIMB 41906, with a tetraploid watermelon plant, of which a representative number of seeds have been deposited under Accession number NCIMB 41905.

Also a method for producing triploid, seedless watermelon fruit is provided, comprising interplanting seed of a triploid bush watermelon plant, representative seeds of which were deposited under Accession number NCIMB 41907 or another bush triploid according to the invention, with a diploid pollenizer plant, allowing pollination of said triploid watermelon plants by pollen of said diploid pollenizer plant to obtain triploid seedless fruits on the triploid plant.

Also a method of producing a triploid watermelon variety having a bush growth type is provided, said method comprising a) providing a diploid bush inbred watermelon line, b) providing a tetraploid bush inbred watermelon line, and c) crossing the diploid and tetraploid bush lines, and collecting the triploid seeds from said cross. In one aspect, the diploid bush inbred watermelon line is the plant representative seeds of which were deposited under Accession number NCIMB41906, or progeny thereof, or vegetative propagations thereof. In another aspect, the tetraploid bush inbred watermelon line is the plant representative seeds of which were deposited under Accession number NCIMB41905, or progeny thereof, or vegetative propagations thereof.

FIGURE LEGENDS

FIG. 1

Schematic diagram of the methods and plants/fruits according to the invention. A bush male (bb) and bush female (bbbb) are crossed to produce seeds of triploid bush hybrids (bbb). These F1 seeds can be interplanted (in-row or between-row) with any diploid pollenizer to produce triploid seedless fruit on the triploid hybrid bush plants.

FIG. 2

Schematic diagram of chromosome 9, showing the area where the bush locus is found on the bottom of chromosome 9 (striped) and the location of SNP1 and SNP2, which are closely linked physically to the bush locus.

The following non-limiting Examples describe the production of triploid bush hybrids according to the invention. Unless stated otherwise in the Examples, methods for conventional watermelon breeding are used, such as e.g.

described in Maynard 2001, Watermelons—Characteristics, Production and Marketing, ASHS Press; Mohr H. C. Watermelon Breeding in Mark J. Bassett (editor) 1986 Breeding Vegetable Crops, AVI Publishing Company.

DEPOSIT INFORMATION

Applicant has deposited hybrid WH3451 at the Dec. 1, 2011 under at the NCIMB under Accession number NCIMB 41907. Seeds of WHAAPD and WHAAOX were deposited by Nunhems B. V. on Dec. 1, 2011 at the NCIMB under Accession numbers NCIMB 41905 and NCIMB 41906, respectively. Access to the deposits will be available during the pendency of this application to persons determined by the Commissioner of Patent and Trademarks to be entitled thereto upon request.

Subject to 37 C.F.R. § 1.808(b), all restrictions imposed by the depositor on the availability to the public of one or more deposits will be irrevocably removed upon the granting of the patent by affording access to a deposit of at least 2500 seeds with the NCIMB Ltd., Ferguson Building, Craibstone Estate, Bucksburn, Aberdeen AB21 9YA, UK. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

EXAMPLES

Example 1: Generation of Triploid Bush Hybrids (Bbb)

It was observed that a home-garden diploid watermelon had an interesting growth type. Starting from this observation a breeding program was developed in order to determine the heritability of this growth type and in order to fix the growth type, as to be able to generate triploid hybrids having this growth type. The growth type was found to be heritable as recessive trait, and was termed "bush allele" (b). It was found to be responsible for vine length, without however affecting leaf size or fruit size.

In order to generate a triploid bush hybrid, first an inbred diploid bush male parent line and an inbred tetraploid bush female parent line were generated (see FIG. 1).

Generation of the inbred bush male parent was done by selecting a diploid having the observed growth type, making a number of crosses with said diploid and proprietary lines and inbreeding the derived diploid bush line for nine generations to fix the bush characteristics in the diploid line.

Generation of the tetraploid female bush inbred line was carried out by selecting a diploid watermelon having the observed growth type, making a number of crosses with said diploid and proprietary lines and generating a diploid bush inbred line by selfing a derived line for more than nine generations to get a uniform (inbred) diploid bush line. The generated inbred diploid bush line was then treated with colchicine for chromosome doubling. After colchicine treatment a tetraploid line was selected and the line was selfed for several generations to fix the bush characteristics in the tetraploid line. In each generation of seed increase of the tetraploid line ploidy level was checked using flow cytometry.

The tetraploid inbred female bush (bbbb), designated WHAAPD, and diploid inbred male bush (bb), designated WHAAOX, were cross-pollinated to produce fruits with triploid seeds (bbb), designated WH3451. Seeds of the triploid hybrid WH3451 were harvested from the fruits and deposited by Nunhems B. V. on Dec. 1, 2011 under at the NICMB under Accession number NCIMB 41907. Seeds of WHAAPD and WHAAOX were deposited by Nunhems B. V. on Dec. 1, 2011 at the NICMB under Accession numbers NCIMB 41905 and NCIMB 41906, respectively.

The physiological and morphological characteristics of the triploid bush hybrid WH3451 were analyzed in the Examples below.

Example 2—Comparison of Triploid Bush Hybrids WH3451 to Prior Art Hybrids 2.1—Materials and Methods A field trial was conducted in Italy (Sant'Agata Bolognese-BO). Seeds were sown on Jul. 4, 2010 and transplanted into the field on 20 May 2010 (100 cm within the row, 250 cm between the rows). The plot contained 10 plants per line.

Ploidy level was determined by flow cytometry.

Mean values were determined for the following characteristics:

Leaf length and leaf widths was measured for 1 leaf of 3 plants per line.

Number of staminate flowers was counted for 3 plants per line on the flowering date. The mean number of 3 plants was calculated.

Mean stem diameter was measured on in the middle of the main stem for 3 plants and the mean was calculated.

Maturity: the number of days from flowering to maturity was determined by recording the dates when the 50% of the plants of the plot showed at least 1 female flower and then when the 50% of the plants of the plot had fruits ready to harvest Stem: average number of internodes: the average number of internodes on the longest vine measured on 3 plants per line Stem: average internode length (cm): the measured average internode length (cm) on the longest vine on 3 plants per line Stem: average length of the longest vine (cm): average length of the longest vine (cm) measured 3 plants per line Average fruit weight (kg): mean of the weight of 3 fruits per line randomly harvested from 3 plants at maturity Average fruit length (cm): mean of the length of 3 fruits Average fruit diameter at mid section (cm): mean of the diameter of 3 fruits Fruit: rind thickness (cm) at the blossom end and rind thickness on the side of the fruit was measured for 3 fruit. Rind thickness is measured from the outer edge of the fruit to the boundary between white mesocarp and colored endocarp.

Fruit: degree Brix: value is the mean of 1 reading for 3 fruits, collected between the centre and the rind of the fruit; expressed in Degrees Brix)(.degree. using the K71901 portable refractometer Mod. RLC ATC 0-18% (OPTECH).

Sowing seed size length (mm) and widths (mm) mean of the measure of 5 seeds colour: evaluated using the Royal Horticultural Society mini colour chart (world wide web at rhs.org.uk/Plants/RHS-Publications/RHS-colour-charts)

2.1—Results

TABLE 1

|  | WH3451 (triploid bush hybrid - invention) | cv Milady Diploid hybrid - normal growth type | cv Fashion F1 Triploid hybrid - normal growth type | cv Boston F1 Triploid hybrid - normal growth type |
|---|---|---|---|---|
| Ploidy | 3n | 2n | 3n | 3n |
| bush alleles | bbb | BB | BBB | BBB |
| Leaf lobes | lobed | lobed | lobed | lobed |
| Leaf length (cm) | 17.50 | 12.17 | 17.13 | 15.67 |
| Leaf width (cm) | 19.50 | 15.50 | 17.97 | 16.30 |
| Leaf colour (RHS color chart) | Dark green RHS 137a | Dark green RHS 137a | Dark green RHS 137c | Dark green RHS 137a |
| Number of staminate flowers | 6.00 | 15.50 | n.d. | n.d. |
| Stem diameter (mm) | 9.00 | 7.00 | 6.25 | 5.50 |
| Number of main stems at crown | 2.00 | 2.50 | 2.00 | 2.50 |
| Leaf: Degree of secondary leaf lobbing 1 = very weak 9 = very strong | 4 | 4 | 4 | 5 |
| Maturity: number of days from flowering to maturity | 27.00 | 29.00 | 29.00 | 32.00 |
| Stem: average number of internodes | 13.57 | 31.36 | 25.95 | 36.53 |
| Stem: average internode length (cm) | 7.00 | 11.00 | 11.00 | 9.00 |
| Stem: average vine length (cm) | 95.00 | 345.00 | 279.00 | 321.00 |
| Ratio: vine length/number of internodes | 7.00 | 11.00 | 11.00 | 9.00 |
| Average fruit weight (kg) | 5.7 | 11.40 | 7.30 | 6.80 |
| Fruit shape in longitudinal section | Broad elliptic (broad circular) | Elongate elliptic | circular | circular |
| Average fruit length (cm) | 24.00 | 46.75 | 20.60 | 23.20 |
| Average fruit diameter at mid section (cm) | 19.00 | 21.25 | 22.25 | 24.55 |
| Fruit index: length/diameter ratio | 1.26 | 2.20 | 0.93 | 0.95 |
| Fruit rind pattern | striped | striped | striped | striped |

TABLE 1-continued

|  | WH3451 (triploid bush hybrid - invention) | cv Milady Diploid hybrid - normal growth type | cv Fashion F1 Triploid hybrid - normal growth type | cv Boston F1 Triploid hybrid - normal growth type |
|---|---|---|---|---|
| Fruit: width of stripes 1 = very narrow 9 = very broad | 5 | 6 | 2 | 2 |
| Fruit: Ground color of skin (RHS color chart) | Medium green RHS 145b | Medium green RHS 145c | Dark green RHS 136a | Light green RHS 2d |
| Fruit: stripe color (RHS color chart) | Dark green RHS 136a | Dark green RHS 137a | Dark green | Dark green RHS 137c |
| Fruit: rind thickness (cm) (blossom end) | 1.50 | 1.00 | 1.00 | 1.30 |
| Fruit: rind thickness (cm) (side) | 2.00 | 2.00 | 1.50 | 1.50 |
| Fruit: Flesh color (RHS color chart) | Dark Red RHS 44a | Dark Red RHS 45a | Dark Red RHS 44a | Dark Red RHS 47a |
| Fruit: degree Brix | 12.00 | 11.00 | 12.00 | 11.75 |
| Sowing seed size 1 = very small, 9 = very large | 2 | 4 | 4 | 5 |
| Sowing seed size length (mm) | 5.00 | 8.00 | 7.00 | 8.00 |
| Sowing seed size width (mm) | 3.00 | 5.00 | 5.00 | 5.00 |

The male (bb) and female (bbbb) bush parents have essentially the same bush growth type characteristics as indicated for the triploid hybrid WH3451 in Table 1 above.

Example 3—Reduced Spacing for Triploid Bush Hybrids

As the triploid bush hybrids are small plants, without however having reduced fruit size and fruit yield per hectare and without having reduced leaf sizes (i.e. photosynthetic tissue), these plants can be used to grow at least about 1.5 times, preferably at least about 2 times or 2.5 times, preferably even about 3 times as many triploid plants per hectare compared to normal-type triploid hybrids, such as Fashion F1 and Boston F1, thereby increasing marketable fruit yield per hectare. Thus, the triploid fruit yield per hectare can be increased significantly using the triploid bush plants according to the invention, i.e. fruit yield from triploid bush plants can be at least about 1.25 times or at least about 1.5 times the yield of a normal type triploid production field.

The following Table 2 shows the number of plants per hectare for the normal growth type triploid varieties Fashion F1 and Boston F1 compared to the triploid bush plants according to the invention, such as WH3451:

|  | Grafted greenhouse | Non-grafted greenhouse | Grafted open field | Non-grafted open field |
|---|---|---|---|---|
| cv Fashion F1 or Boston F1 | 2500 plants/ha | 5000 plants/ha | 3000 plants/ha | 7000 plants/ha |
| Triploid bush hybrid | 7500 plants/ha | 15000 plants/ha | 6000-8000 plants/ha | 12000-150000 plants/ha |

Fruit yields for Fashion F1 and Boston F1 are about 60 tonnes/hectare (t/ha) in the open field compared to about 75-90 t/ha for the triploid bush hybrid.

Example 3

In 2012 the vegetative growth type of the male (bb) and female (bbbb) bush parents was determined, the results of which are shown in Table 3.

TABLE 3

|  | NCIMB41905 (tetraploid bush) | NCIMB41906 (diploid bush) |
|---|---|---|
| Ploidy | 4n | 2n |
| bush alleles | bbbb | bb |
| Leaf lobes | lobed | lobed |
| Leaf length (cm) | 13.00 | 14.00 |
| Leaf width (cm) | 15.00 | 10.00 |
| Leaf colour (RHS color chart) | Dark green RHS 137c | Dark green RHS 137c |
| Stem: average internode length (cm) | 6.00 | 6.00 |
| Stem: average vine length (cm) | 133.00 | 150.00 |
| Ratio: vine length/ number of internodes | 6.00 | 6.00 |

Example 4

The locus of the recessive bush allele (b) was mapped to the bottom of chromosome 9, physically close to two single nucleotide polymorphism markers (SNPs) called herein SNP1 and SNP2, shown in Table 4 and Table 5 below. See also FIG. 2, showing SNP1 and SNP2 and the region in which the bush locus is located (indicated by the striped area).

The bush locus was mapped in three different steps:

1) QTL mapping on five F2 populations

2) Increasing marker density with Whole Genome reSequencing (WGrS)

3) Association study of bush haplotypes over germplasm

Step 1, QTL Mapping

QTL mapping was performed in four populations that segregated for the bush phenotype. The F2 populations, 188 individuals each, were derived from three-way crosses between a bush hybrid and a non-bush inbred line. The four hybrid donor parents were homozygous for the bush trait and share the same trait source, while differing in elite background genetics.

Bush phenotypes were observed from the F2 plants. The phenotype is clearly distinguishable by the breeders' eye in young plants.

Based on prescreening results on population parents, one of the four populations was selected for QTL mapping with a genome-wide SNP marker selection. This resulted in a major locus for the bush trait mapped to chromosome 9. Additional markers were selected around the QTL peak to reduce the interval to approximately 100 cM, with three markers showing good linkage to the trait locus (LOD 28-30, 50-52% explained variance). The markers were validated over the three remaining populations. However, the markers found with QTL mapping to be linked most to the bush locus did not work in all four populations and marker density was limited in the area around the locus. This problem was solved by resorting to a WGrS approach in step 2.

Step 2)

To increase marker density around the bush locus, five pooled DNA samples were subjected to WGrS against the watermelon reference genome (Guo et al., 2013, supra). Pools were created from phenotypic bush and non-bush plant selections from two populations. In a physical area of about 600 kbp we identified genotypes associated with the bush phenotype. SNP assays were ordered and validated over the four F2 populations mentioned in step 1. Two markers, referred to as SNP1 and SNP2, were highly linked to the bush phenotype in all four F2 populations.

Step 3)

The two SNP markers SNP1 and SNP2 were validated in a full-sib F2 population from a cross between a bush parent and a non-bush elite parent and phenotyped for bush.

TABLE 4

| | Chromosome | Nucleotide position | Sequence |
|---|---|---|---|
| SNP1 | 9 | 30.382.688 | cacccttacctaatttcctcattcc tttttctgtcagttctcttcctcact atcattttcctttcttcttcttctt [C/T]ttcttcttcttcttcttcggt tggggactaaactagaagtagaccca attctttattattgtgtgttgttatg gg (SEQ ID NO: 1) |
| SNP2 | 9 | 30.770.924 | tagggttttcatcttttcatccag ttttatctcgacttaattcttttggc ttccaaaacttatttcttcata [A/G]taactaaaaactactagttaa cacatcaaatctaataaaaaattcct agattagaagcataagtgttttcaa tg (SEQ ID NO: 2) |

TABLE 5

|  | NCIMB41906 (bb) | NCIMB41905 (bbbb) | NCIMB41907 (bbb) | Diploid plant with a normal growth type (BB) |
|---|---|---|---|---|
| SNP1 genotype | TT | TTTT | TTT | CC |
| SNP2 genotype | AA | AAAA | AAA | GG |

Genotyping Assays for SNP1 and SNP2

A KASP assay was developed for SNP1

| SNP ID. | SNP1 | Interpretation |
|---|---|---|
| Allele call FAM | C | "normal" |
| Allele call VIC | T | "bush" |
| Primer_AlleleFAM | GAAGGTGACCAAGTTCATGCTCCAACCGAAGAAGAAGAAGAAG | |
| Primer_AlleleVIC | GAAGGTCGGAGTCAACGGATTCCCAACCGAAGAAGAAGAAGAAA | |
| Primer_Common | TCTGTCAGTTCTCTTCCTCACTATCATTT | |

Using this assay three plant genotypes and phenotypes can be distinguished:

| CC | Non-bush phenotype (BB) |
|---|---|
| CT | Non-bush phenotype (Bb), but heterozygous for the recessive bush allele |
| TT | bush-phenotype (homozygous bb) |

A KASP assay was developed for SNP2

| SNP ID. | SNP2 | Interpretation |
|---|---|---|
| Allele call FAM | A | "bush" |
| Allele call VIC | G | "non-bush" |
| Primer_AlleleFAM | GAAGGTGACCAAGTTCATGCTGATTTGATGTGTTAACTAGTAGTTTTTAGTTAT | |
| Primer_AlleleVIC | GAAGGTCGGAGTCAACGGATTTGATGTGTTAACTAGTAGTTTTTAGTTAC | |
| Primer_Common | CGACTTAATTCTTTTGGCTTCCAAAACTTA | |

Using this assay three plant genotypes and phenotypes can be distinguished:

| GG | Non-bush phenotype (BB) |
|---|---|
| AG | Non-bush phenotype (Bb), but heterozygous for the recessive bush allele |
| AA | bush-phenotype (homozygous bb) |

The invention claimed is:

1. A plant of the species *Citrullus lanatus*, wherein said plant is triploid and comprises three copies of a recessive allele designated bush, which allele is linked to a thymine (T) at nucleotide 76 of SEQ ID NO: 1 and to an adenine (A) at nucleotide 76 of SEQ ID NO: 2, wherein said bush allele is present in seeds having been deposited under accession number NCIMB 41907, and wherein the plant comprises an average internode length on the longest vine of 4.7 cm to 7 cm and an average longest vine length of not longer than 140 cm, wherein the average leaf size and fruit size of said plant is not reduced compared to a triploid plant comprising three copies of the wild type Bush allele when grown under the same environmental conditions.

2. The plant according to claim 1, wherein the plant is an F1 hybrid produced from a cross between a diploid inbred male parent line comprising two copies of a recessive allele designated bush, which allele is linked a thymine (T) at nucleotide 76 of SEQ ID NO: 1 and to an adenine (A) at nucleotide 76 of SEQ ID NO: 2, and a tetraploid inbred parent line, comprising four copies of a recessive allele designated bush, which allele is linked to a thymine (T) at nucleotide 76 of SEQ ID NO: 1 and to an adenine (A) at nucleotide 76 of SEQ ID NO: 2.

3. The plant according to claim 1, wherein the plant has a longest vine length of not longer than 100 cm.

4. The plant according to claim 1, wherein said plant has not more than 15 internodes on the longest vine.

5. The plant according to claim 1, wherein the ratio of longest vine length:number of internodes on the longest vine is 7 or less.

6. The plant according to claim 1, wherein said plant has a stem diameter of at least 8 mm.

7. The plant according to claim 1, wherein said plant comprises leaves of at least 10 cm long and at least 15 cm wide.

8. The plant according to claim 1, wherein said plant produces fruits with an average fruit weight of at least 5 kg after pollination with diploid pollen.

9. Seeds from which a plant according to claim 1 can be grown.

10. A plant or seed of the species *Citrullus lanatus* wherein said plant is tetraploid and comprises four copies of a recessive allele designated bush, which allele is linked to a thymine (T) at nucleotide 76 of SEQ ID NO: 1 and to an adenine (A) at nucleotide 76 of SEQ ID NO: 2, wherein said bush allele is present in seeds having been deposited under accession number NCIMB 41905, wherein the plant comprises an average internode length on the longest vine of 4.7 cm to 7 cm and an average longest vine length of not longer than 140 cm, wherein the average leaf size and fruit size of said plant is not reduced compared to a tetraploid plant comprising four copies of the wild type Bush allele when grown under the same environmental conditions.

11. A tissue culture of regenerable cells of a plant of claim 10.

12. A tissue culture according to claim 11, comprising cells or protoplasts or plant tissue from a plant part, wherein the plant part is an embryo, a meristem, a cotyledon, pollen, an ovule, a leaf, an anther, a root, a root tip, pistils, a flower, seed, or a stem.

13. A plant part of the plant according to claim 1, wherein said part is a scion, fruit, pollen, ovule, stem, cotyledon, leaf, cell, embryo, meristem, anther, root, root tip, pistil, flower, or seed.

14. A watermelon plant regenerated from the tissue culture of claim 11, wherein the regenerated plant is a tetraploid and comprises the bush allele.

15. A method for producing triploid hybrid watermelon seeds, wherein plants grown from such seeds comprise three copies of a recessive allele designated bush, said method comprising: a) providing a diploid watermelon plant comprising two copies of a recessive allele designated bush and a tetraploid plant comprising four copies of a recessive allele designated bush, b) allowing pollination of flowers of the tetraploid bush plant with pollen of the diploid bush plant, and c) harvesting seeds produced in the fruits of the tetraploid plant,
wherein the bush allele is linked to a thymine (T) at nucleotide 76 of SEQ ID NO: 1 and to an adenine (A) at nucleotide 76 of SEQ ID NO: 2, and wherein the average leaf size and fruit size of said plants grown from the triploid hybrid watermelon seeds are not reduced compared to a triploid plant comprising three copies of the wild type Bush allele when grown under the same environmental conditions.

16. The method according to claim 15, wherein said tetraploid plant has the following characteristics: a longest vine length of not more than 100 cm, an average internode length on the longest vine of 7 cm or less but at least 4.7 cm, and produces leaves of at least 10 cm long and at least 15 cm wide.

17. A method for seedless triploid watermelon fruit production, said method comprising: (a) providing triploid hybrid watermelon plants each comprising three copies of a recessive allele designated bush, (b) interplanting said triploid hybrid plants with diploid pollenizer plants, (c) harvesting the seedless watermelon fruits produced on the triploid plants of (a),
wherein the bush allele is linked to a thymine (T) at nucleotide 76 of SEQ ID NO: 1 and to an adenine (A) at nucleotide 76 of SEQ ID NO: 2, and wherein the average leaf size and fruit size of said triploid plant is not reduced compared to a triploid plant comprising three copies of the wild type Bush allele when grown under the same environmental conditions.

18. The method according to claim 17, wherein at least 1.5 times more triploid plants are grown per hectare than when a triploid hybrid plant comprising three copies of the wild type Bush allele is used.

19. The method according to claim 18, wherein at least 15% more triploid fruits are produced per hectare than when a triploid hybrid plant comprising three copies of the wild type Bush allele is used.

20. A tissue culture of regenerable cells of a plant of claim 1.

21. A watermelon plant regenerated from the tissue culture of claim 20, wherein the regenerated plant is a triploid and comprises the bush allele.

* * * * *

```
                         SEQUENCE LISTING

<160> NUMBER OF SEQ ID NOS: 2

<210> SEQ ID NO 1
<211> LENGTH: 151
<212> TYPE: DNA
<213> ORGANISM: watermelon

<400> SEQUENCE: 1 cacccttttac ctaatttcct cattcctttt tctgtcagtt ctcttcctca ctatcatttt    60 tccttttcttc ttcttttttct tcttcttctt cttcggttgg ggactaaact agaagtagac   120
ccaattcttt attattgtgt gttgttatgg g                                   151

<210> SEQ ID NO 2
<211> LENGTH: 151
<212> TYPE: DNA
<213> ORGANISM: watermelon

<400> SEQUENCE: 2
tagggttttt catcttttc atccagtttt atctcgactt aattcttttg gcttccaaaa     60
cttattttct tcataataac taaaaactac tagttaacac atcaaatcta ataaaaaatt    120
cctagattag aagcataagt gttttttcaat g                                  151
```